United States Patent
Coppes et al.

(10) Patent No.: US 8,568,483 B2
(45) Date of Patent: Oct. 29, 2013

(54) MODULAR INTERVERTEBRAL IMPLANT

(75) Inventors: Justin Coppes, Downingtown, PA (US); Jeffrey Walker, West Chester, PA (US); David Nichols, West Chester, PA (US); Curtis Compton, Downingtown, PA (US); Vincent Mandes, Horsham, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 729 days.

(21) Appl. No.: 12/522,616

(22) PCT Filed: Jan. 14, 2008

(86) PCT No.: PCT/US2008/000457
§ 371 (c)(1),
(2), (4) Date: Jul. 9, 2009

(87) PCT Pub. No.: WO2008/088777
PCT Pub. Date: Jul. 24, 2008

(65) Prior Publication Data
US 2010/0280617 A1 Nov. 4, 2010

Related U.S. Application Data

(60) Provisional application No. 60/884,680, filed on Jan. 12, 2007.

(51) Int. Cl.
*A61F 2/44* (2006.01)
(52) U.S. Cl.
USPC ........................................ 623/17.16

(58) Field of Classification Search
USPC ............... 623/17.11–17.16; 606/246–279
See application file for complete search history.

(56) References Cited

U.S. PATENT DOCUMENTS

| 5,108,442 | A | 4/1992 | Smith | |
|---|---|---|---|---|
| 5,314,477 | A | 5/1994 | Marnay | |
| 6,936,071 | B1 * | 8/2005 | Marnay et al. | 623/17.15 |
| 7,153,325 | B2 * | 12/2006 | Kim et al. | 623/17.15 |
| 7,204,852 | B2 | 4/2007 | Marnay et al. | |
| 7,235,101 | B2 * | 6/2007 | Berry et al. | 623/17.11 |
| 7,291,173 | B2 * | 11/2007 | Richelsoph et al. | 623/17.13 |
| 7,491,204 | B2 | 2/2009 | Marnay et al. | |
| 7,563,286 | B2 | 7/2009 | Gerber et al. | |

(Continued)

FOREIGN PATENT DOCUMENTS

| CN | 101588773 | 11/2009 |
|---|---|---|
| EP | 1527759 A1 | 4/2005 |

(Continued)

OTHER PUBLICATIONS

International Patent Application No. PCT/US2008/00457: International Search Report dated May 16, 2008, 1 page.
European Patent Application No. EP08705584: Supplementary European Search Report dated Dec. 3, 2012, 8 pages.

*Primary Examiner* — Kevin T Truong
*Assistant Examiner* — Christopher Beccia
(74) *Attorney, Agent, or Firm* — Woodcock Washburn LLP

(57) ABSTRACT

An intervertebral implant component includes an inlay which fits into an endplate, where the inlay is prevented from moving relative to the endplate. Various embodiments of locking mechanisms for preventing movement are disclosed. In some preferred embodiments, a surgeon is able to see that the locking mechanism is properly engaged.

32 Claims, 29 Drawing Sheets

(56) References Cited

U.S. PATENT DOCUMENTS

| | | | |
|---|---|---|---|
| 7,637,956 B2 * | 12/2009 | Lechmann et al. | 623/17.15 |
| 7,763,024 B2 | 7/2010 | Bertagnoli et al. | |
| 7,887,590 B2 | 2/2011 | Levieux | |
| 7,887,592 B2 * | 2/2011 | Koske | 623/17.15 |
| 7,909,877 B2 * | 3/2011 | Krueger et al. | 623/17.15 |
| 7,927,373 B2 * | 4/2011 | Parsons et al. | 623/17.14 |
| 7,927,374 B2 * | 4/2011 | Duggal et al. | 623/17.14 |
| 2005/0251260 A1 * | 11/2005 | Gerber et al. | 623/17.13 |
| 2005/0267581 A1 * | 12/2005 | Marnay et al. | 623/17.14 |
| 2006/0149371 A1 * | 7/2006 | Marik et al. | 623/17.11 |
| 2006/0190082 A1 * | 8/2006 | Keller et al. | 623/17.11 |
| 2010/0082110 A1 | 4/2010 | Belliard | |

FOREIGN PATENT DOCUMENTS

| | | |
|---|---|---|
| EP | 2101693 | 9/2009 |
| FR | 2887435 A1 | 12/2006 |
| JP | 2005-137905 | 6/2005 |
| JP | 2006-214559 | 8/2006 |
| WO | WO 2004/016217 | 2/2004 |
| WO | WO 2006/057698 A1 | 6/2006 |
| WO | WO 2006/120505 A1 | 11/2006 |
| WO | WO 2008/088777 | 7/2008 |
| ZA | 2009/04702 | 4/2010 |

* cited by examiner

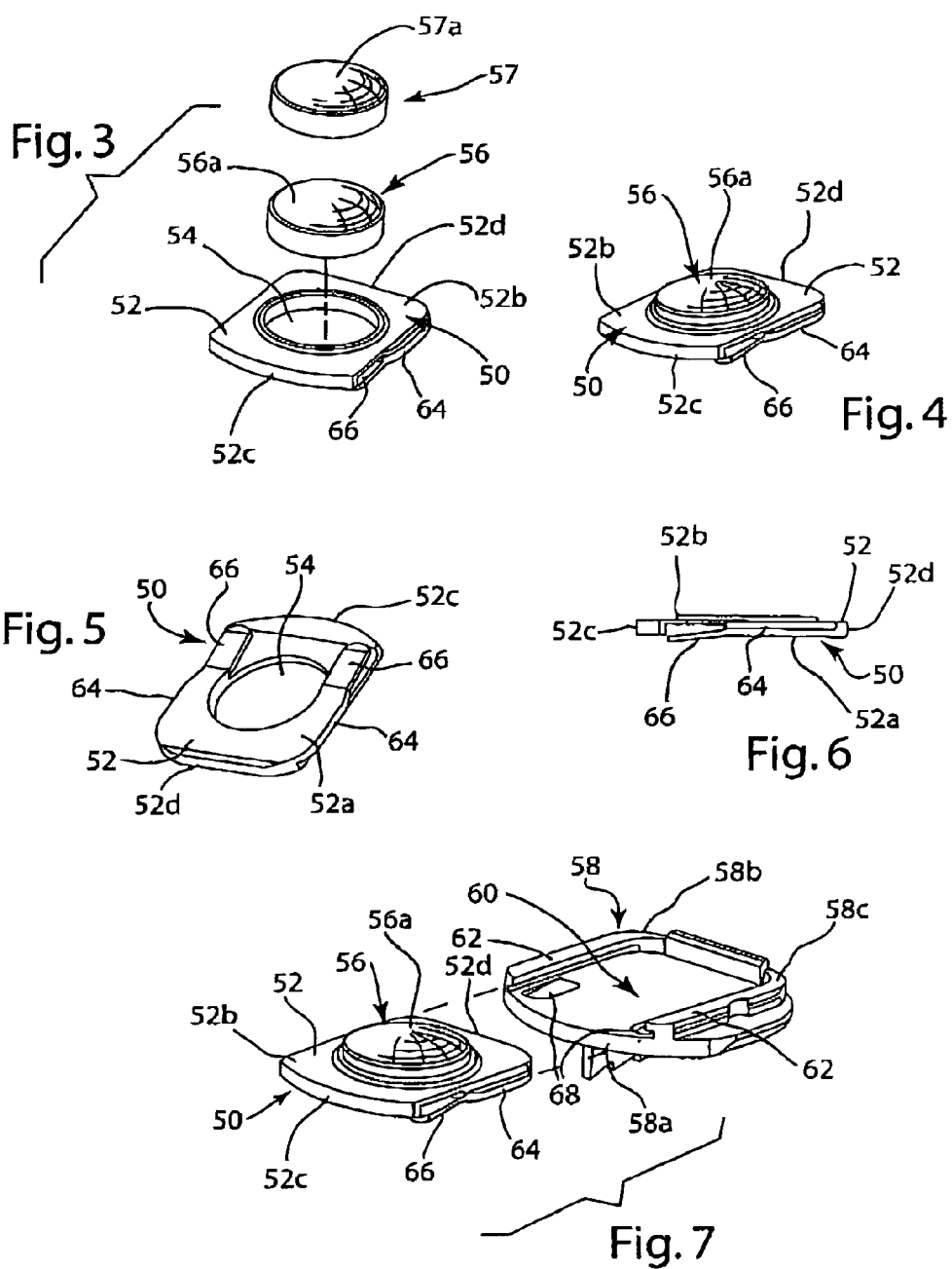

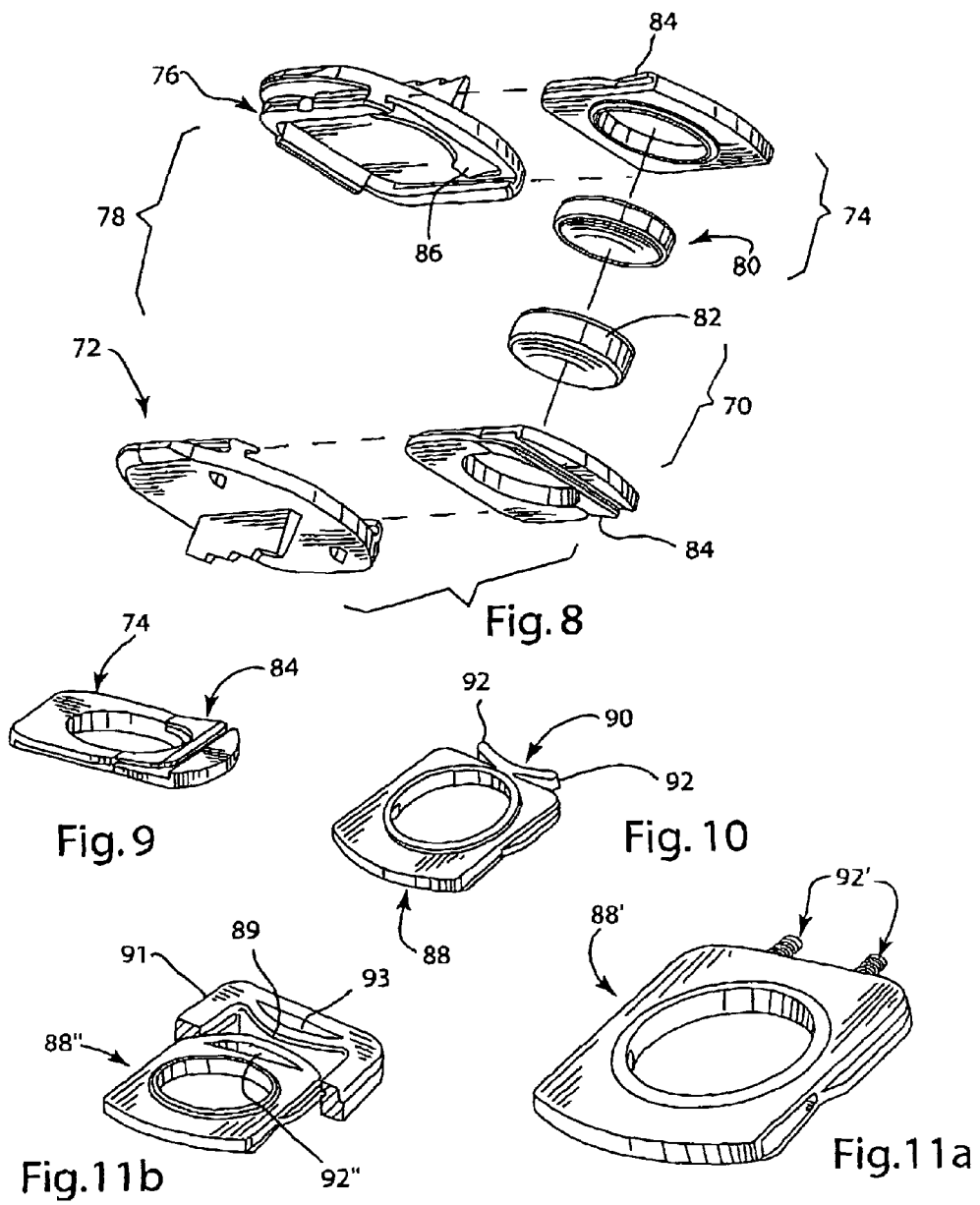

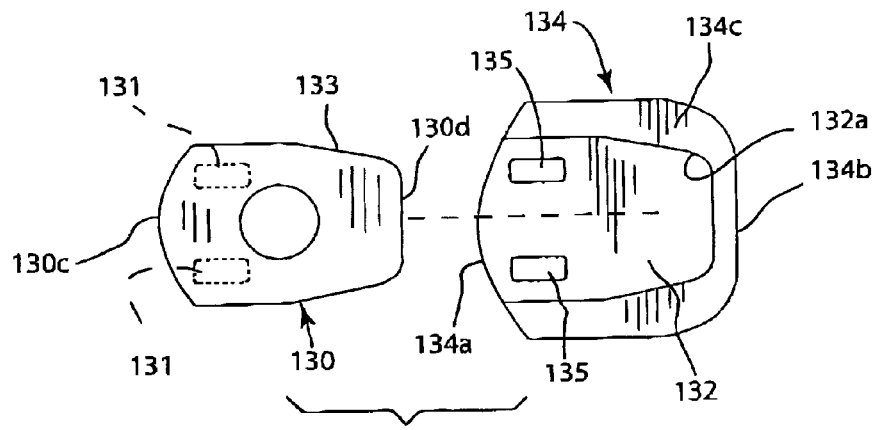
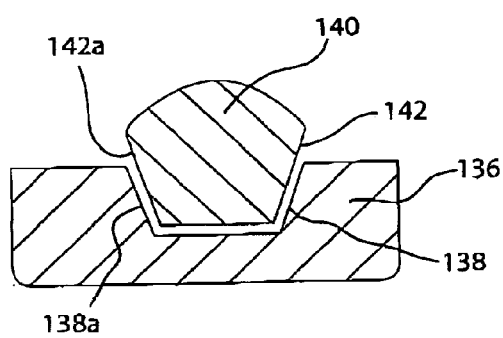
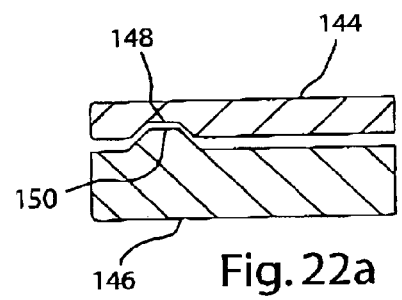
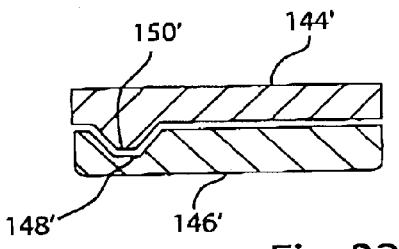
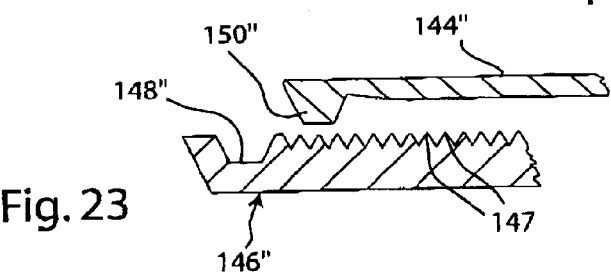

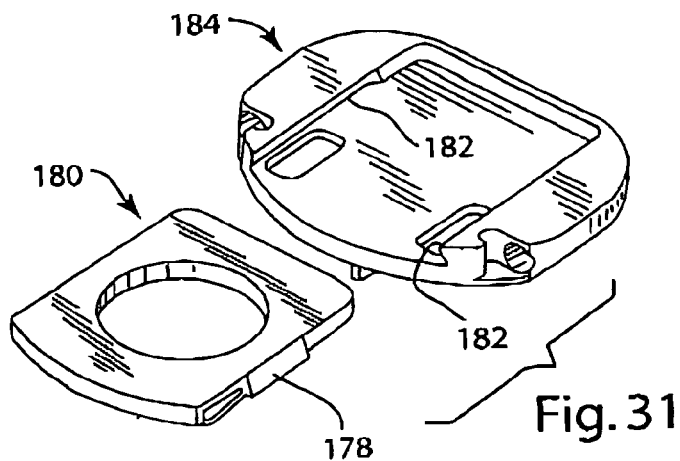
Fig. 31
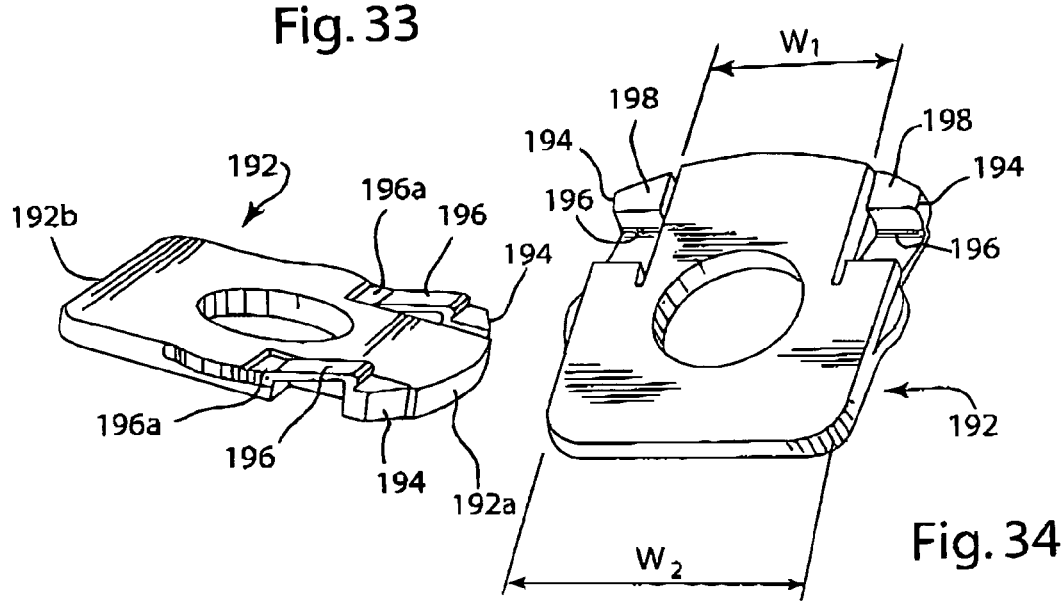
Fig. 33
Fig. 34

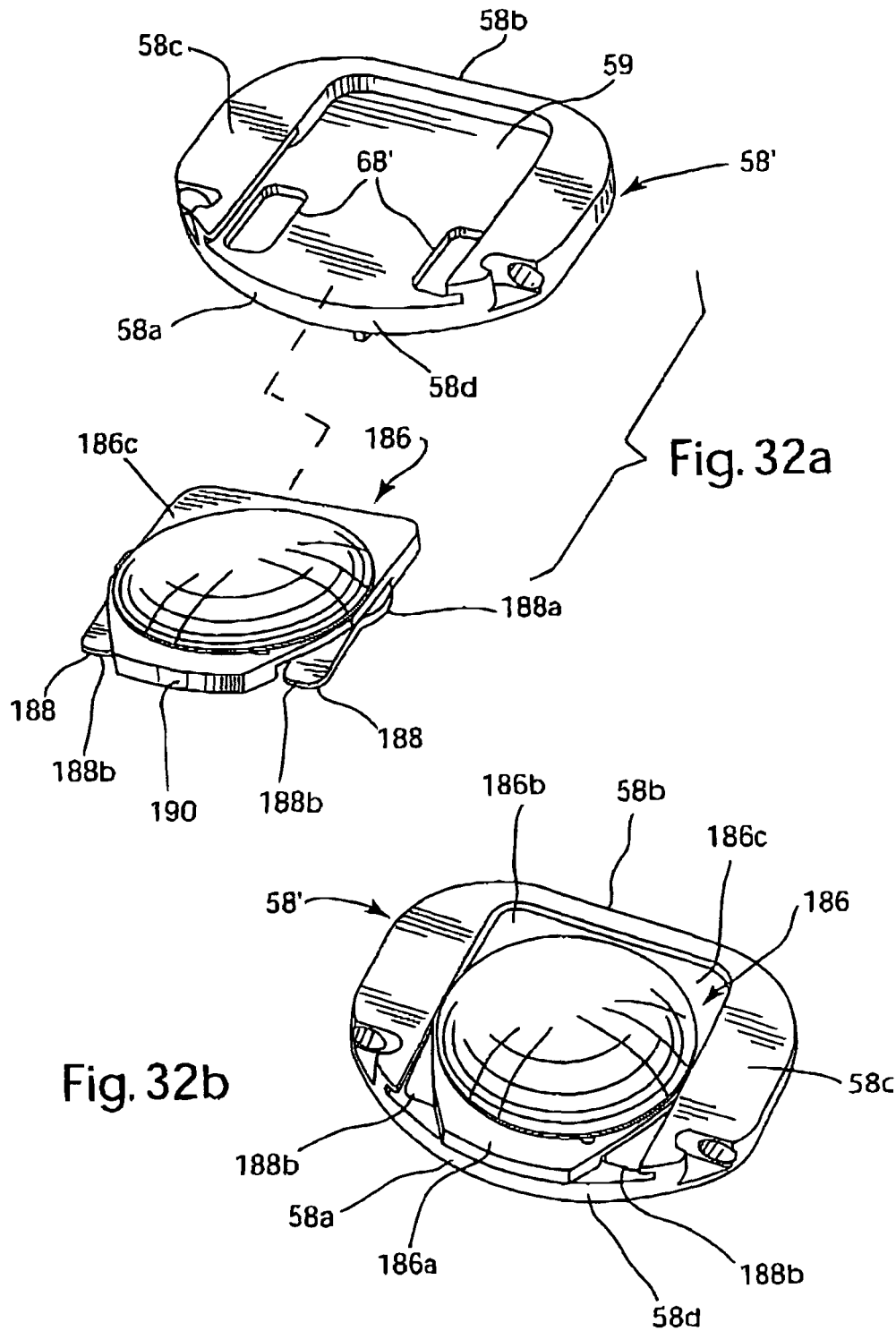

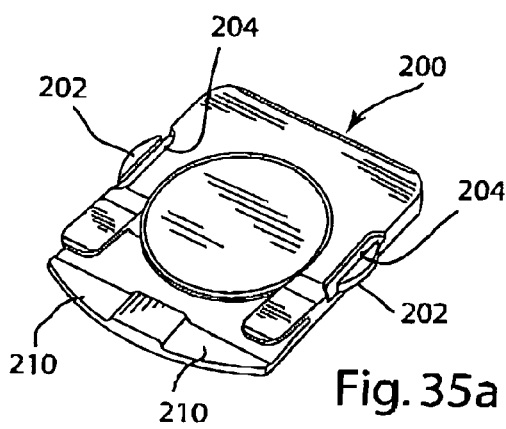
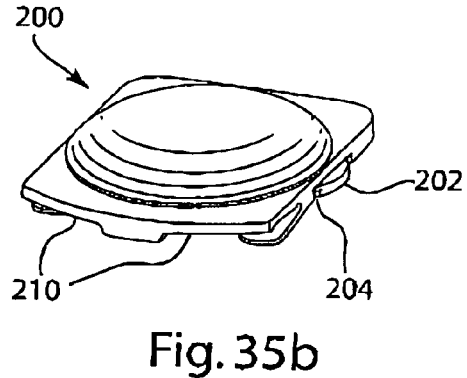
Fig. 35a  Fig. 35b
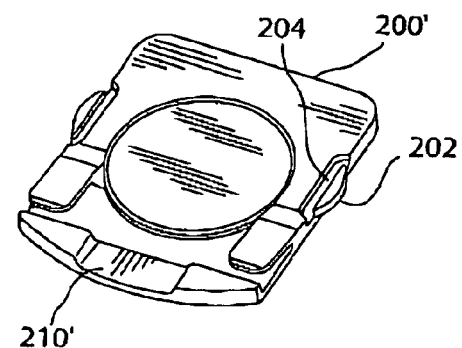
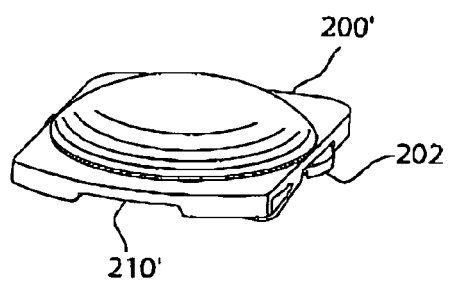
Fig. 36a  Fig. 36b
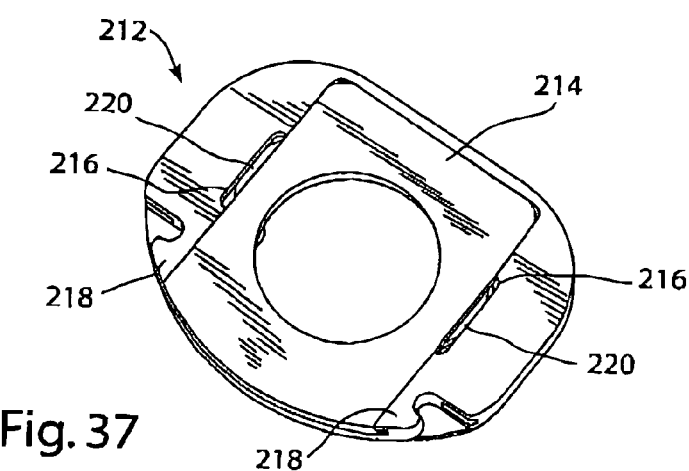
Fig. 37

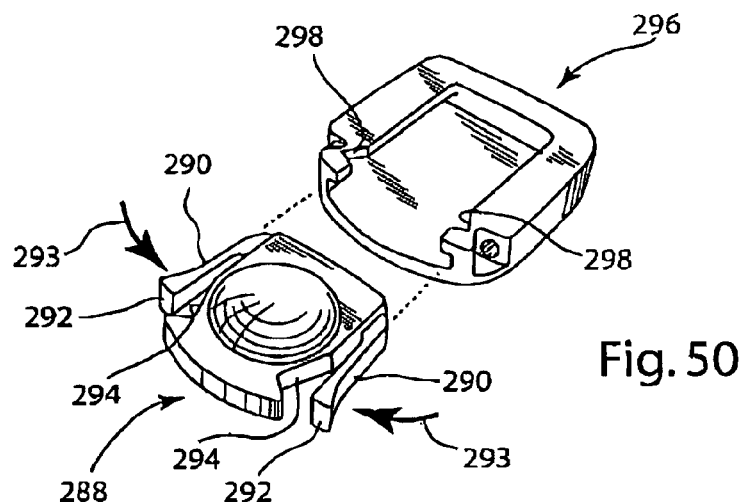
Fig. 50
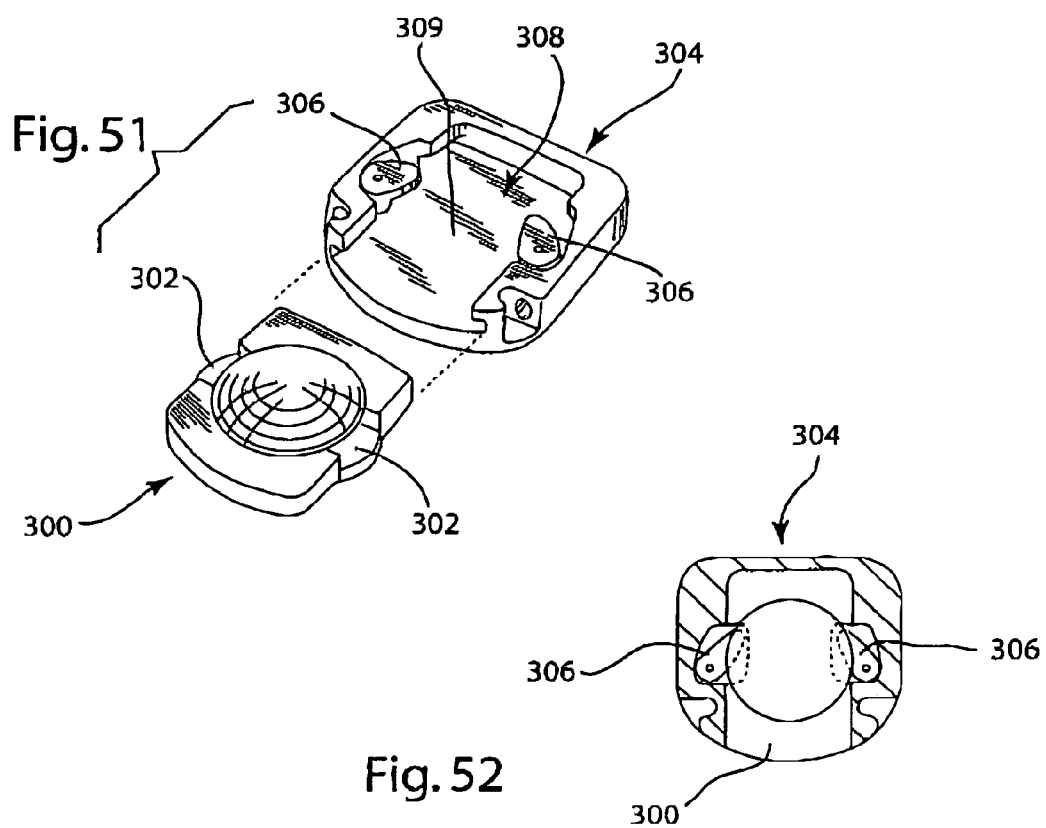
Fig. 51
Fig. 52

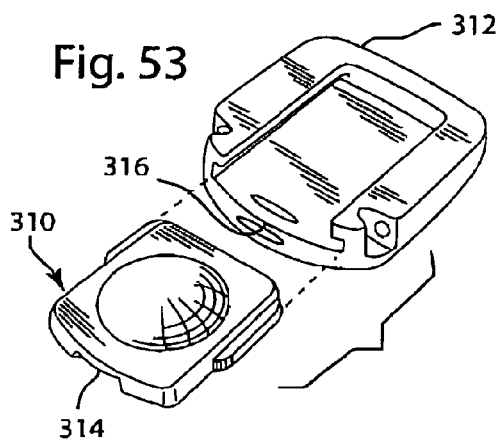
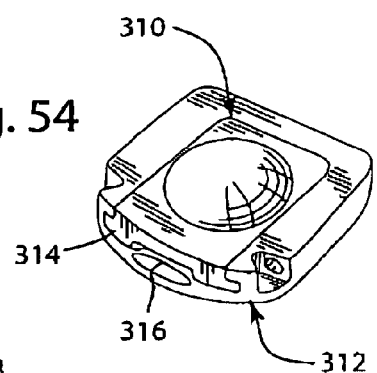
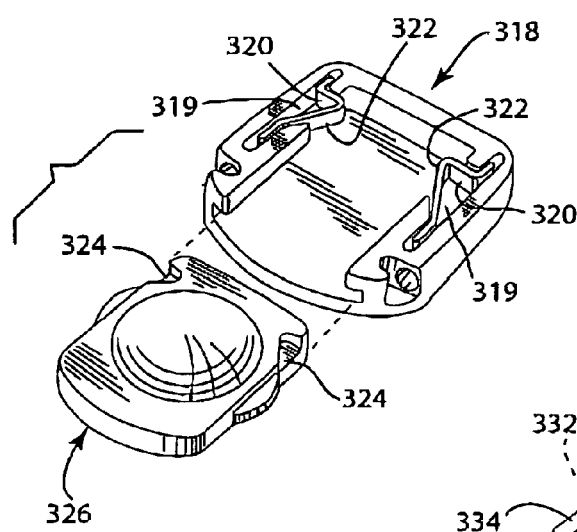
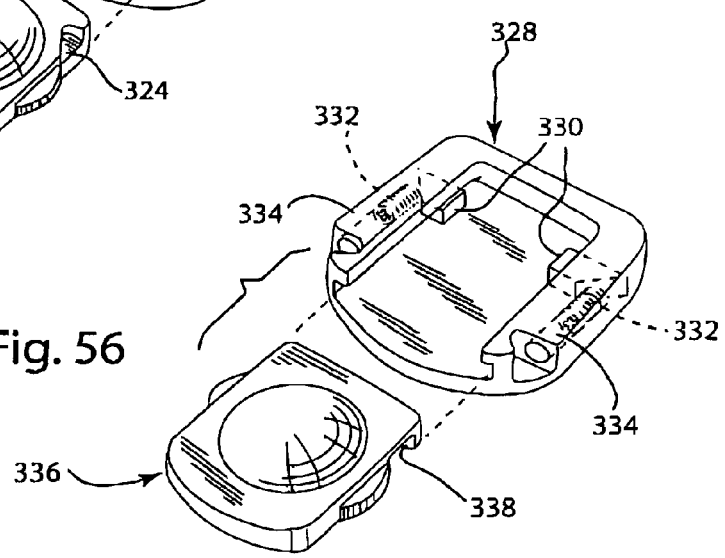

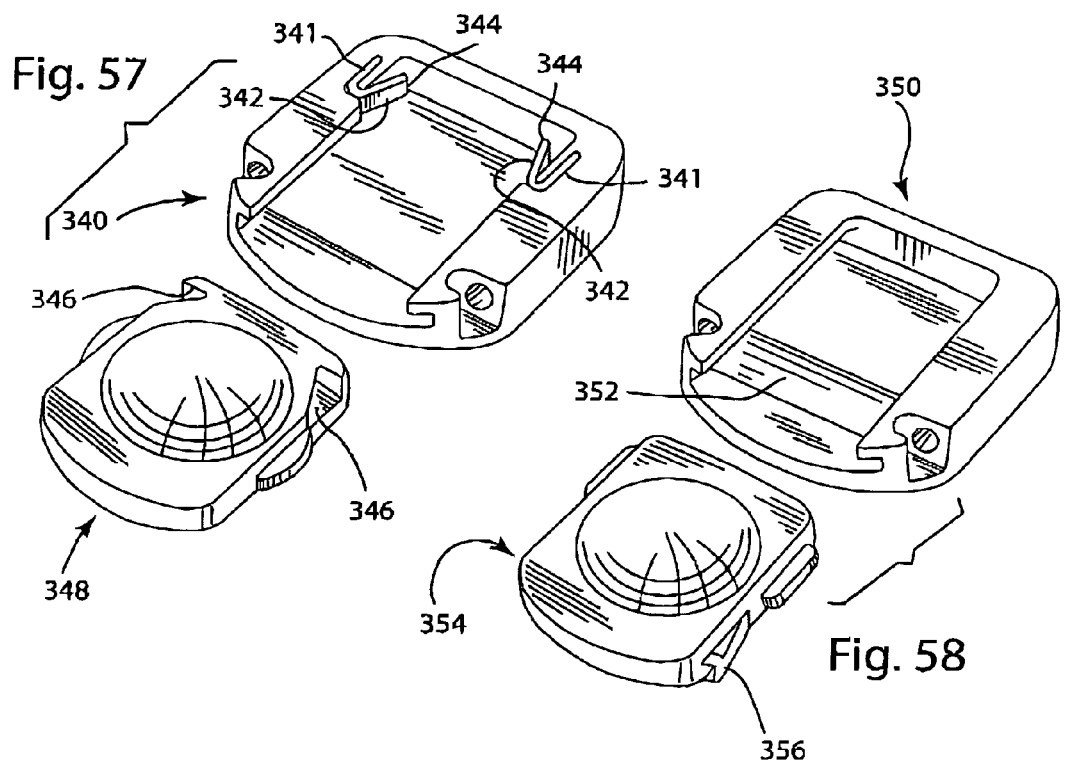
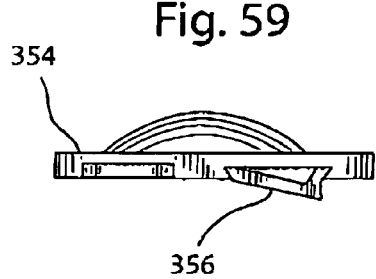
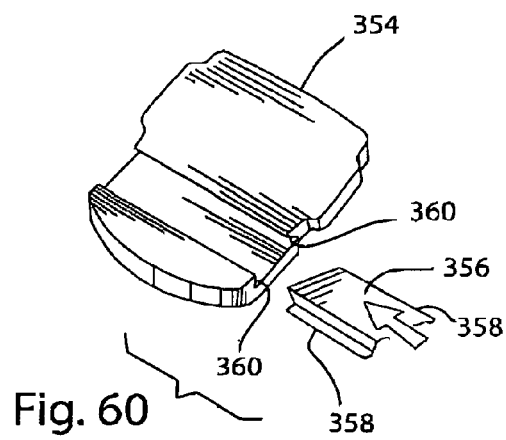

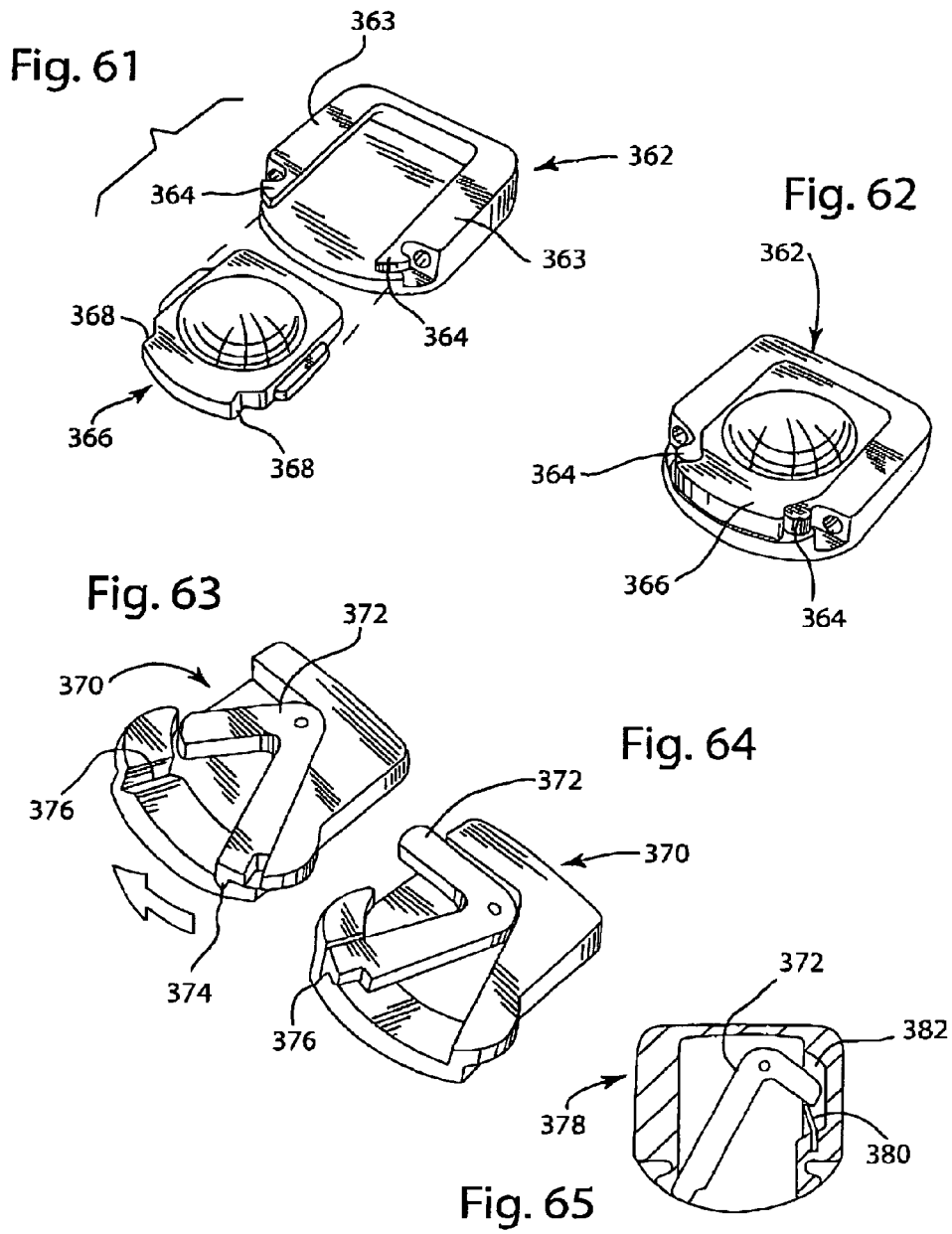

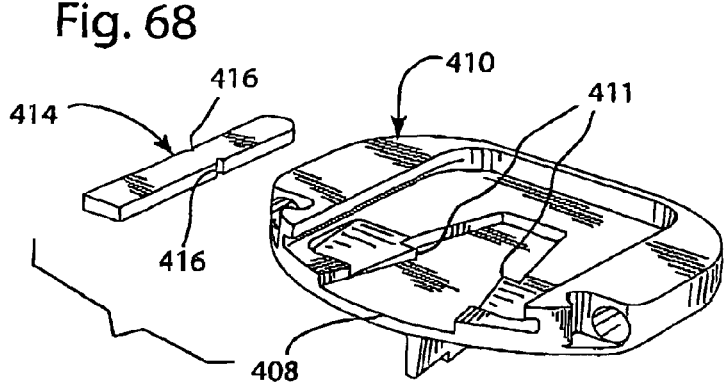
Fig. 68
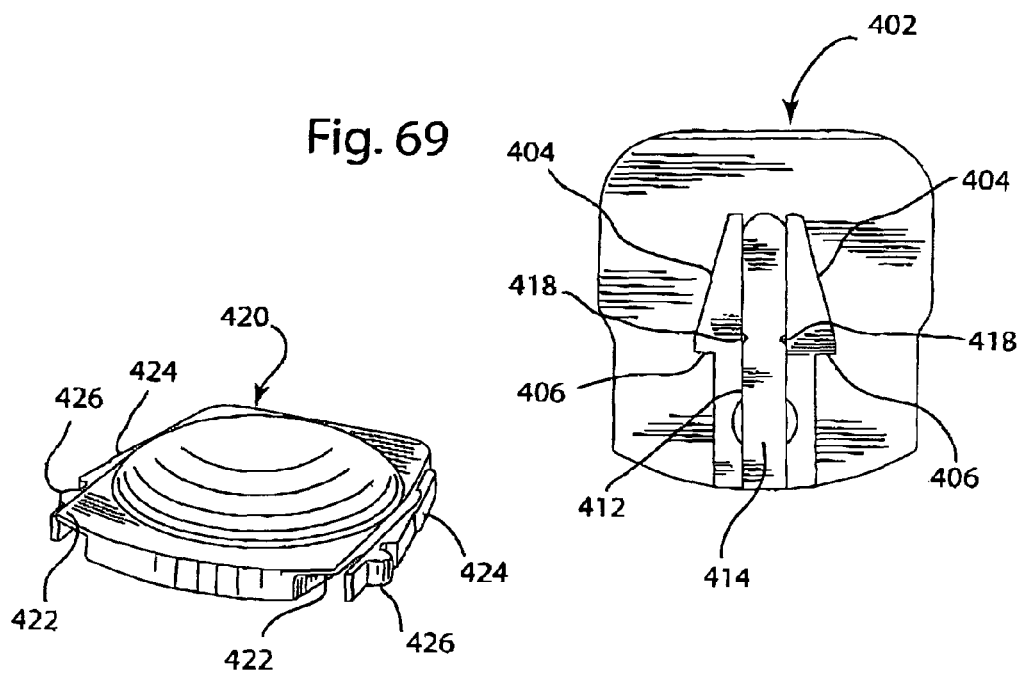
Fig. 69
Fig. 70

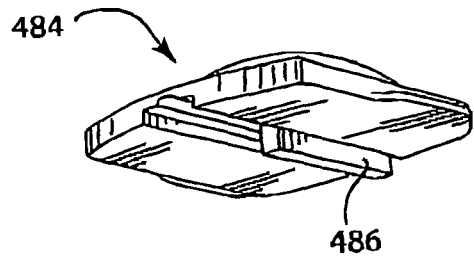
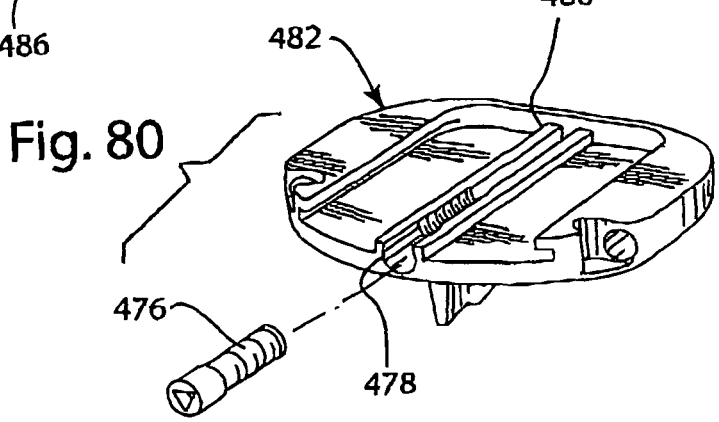
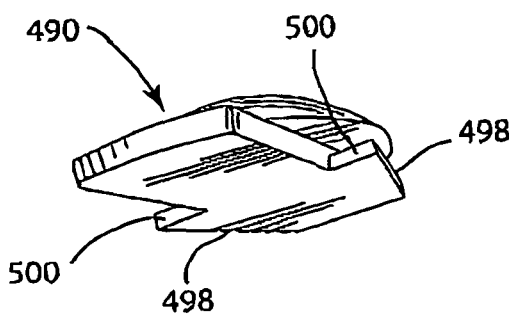
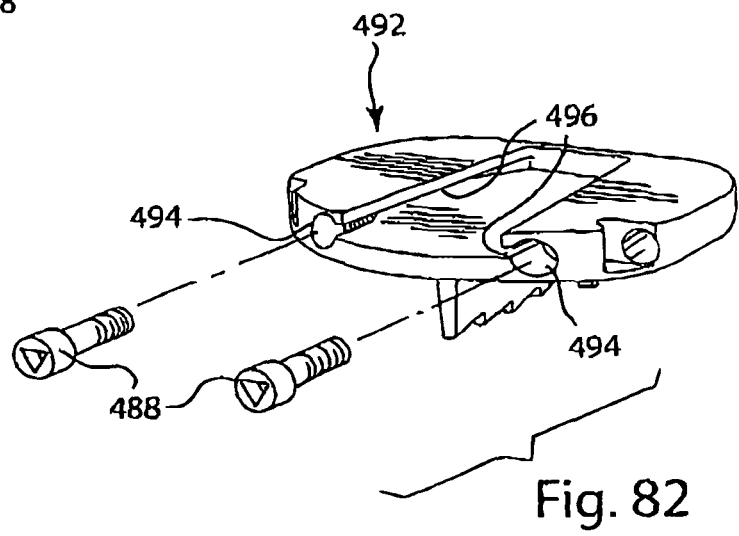
Fig. 79
Fig. 80
Fig. 81
Fig. 82

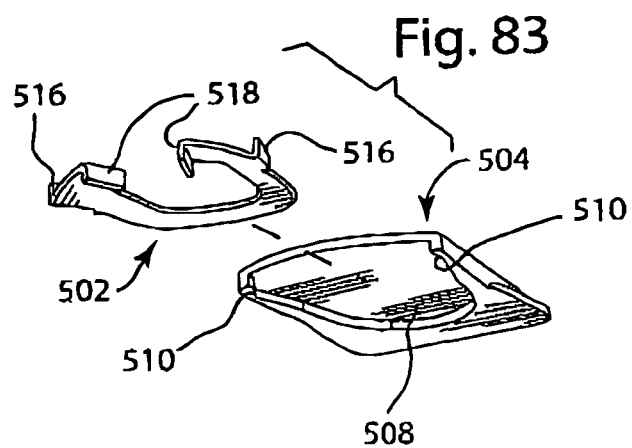
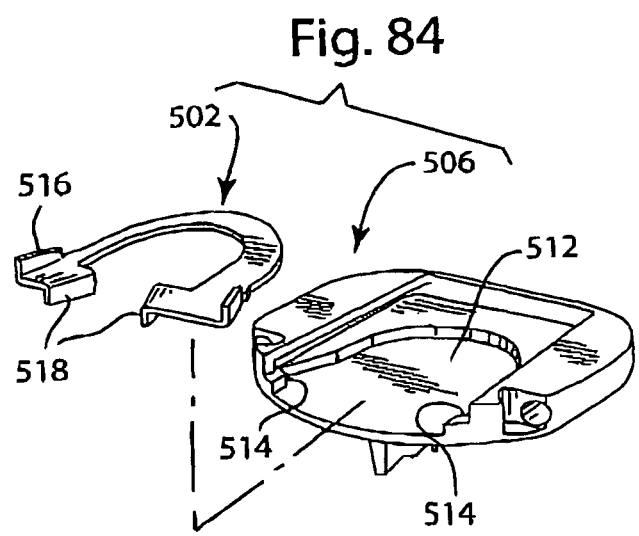

MODULAR INTERVERTEBRAL IMPLANT

CROSS-REFERENCE TO RELATED APPLICATIONS

This application is the National Stage of International Application No. PCT/US2008/000457, filed Jan. 14, 2008, which claims the benefit of U.S. Provisional Application No. 60/884,680 filed Jan. 12, 2007, the disclosures of which are incorporated herein by reference in their entirety.

BACKGROUND OF THE INVENTION

Historically, when it was necessary to completely remove a disc from between adjacent vertebrae, the conventional procedure was to fuse the adjacent vertebrae together creating a situation where no motion is present between the spinal segments. This "spinal fusion" procedure, which is still in use today, is a widely accepted surgical treatment for symptomatic lumbar and cervical degenerative disc disease.

More recently, there have been developments in the field of disc replacement, namely disc arthoplasty, which involves the insertion of an artificial intervertebral disc implant into the intervertebral space between adjacent vertebrae. Such a disc implant allows limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. In contrast with fusion techniques, total disc replacement generally preserves mobility in the motion segment and mimics physiologic conditions.

One such intervertebral implant includes an upper part that can communicate with an adjacent vertebrae, a lower part that can communicate with an adjacent vertebrae, and an insert located between these two parts. To provide an anchor to the adjacent vertebrae, each part includes a vertically extending keel. Examples of this type of implant are disclosed in U.S. Pat. No. 5,314,477 (Marnay), U.S. Pat. No. 6,936,071 (Marnay et al.), and U.S. Pat. No. 7,204,852 (Marnay et al.), which are hereby incorporated by reference.

It will also be noted that in order to provide a keel slot in a vertebra, a cutting of the bone needs to be performed. Typically the cut is made by chiseling, drilling or milling. Combinations of these procedures are possible too. Exemplary of such prior art devices and methods are those disclosed in USPA 2004-0215198 (Marnay et al.) and USPA 2006-0064100 Bertagnoli et al.), which are hereby incorporated by reference.

BRIEF SUMMARY OF THE INVENTION

In accordance with the present invention, an intervertebral implant component includes an inlay which fits into an endplate, where the inlay is prevented from moving relative to the end plate. Various embodiments of locking mechanisms for preventing movement are disclosed. In some preferred embodiments, a surgeon is able to see that the locking mechanism is properly engaged.

It will also be appreciated that various combinations of the features disclosed hereafter for one embodiment may also be useful with other embodiments, as desired.

Other features and advantages of the present invention are stated in or apparent from detailed descriptions of presently preferred embodiments of the inventions found hereinbelow.

BRIEF DESCRIPTION OF THE SEVERAL VIEWS OF THE DRAWINGS

FIG. 3 is an exploded top perspective view of an alternative inlay with a ramp locking mechanism according to the present invention.

FIG. 4 is a perspective view of the inlay of FIG. 3 with the insert in place.

FIG. 5 is a bottom perspective view of the inlay depicted in FIG. 3.

FIG. 6 is a side view of the inlay depicted in FIG. 5.

FIG. 7 is a top perspective view of the inlay of FIG. 3 being inserted into an endplate.

FIG. 8 is an exploded bottom perspective view of an alternative ramp locking mechanism for an inlay.

FIG. 9 is a top perspective view of the inlay depicted in FIG. 8.

FIG. 10 is a top perspective view of an alternative inlay with a rear spring mechanism.

FIG. 11a is a top perspective view of an alternative inlay with a rear spring mechanism.

FIG. 11b is a top perspective view of another alternative inlay with a rear spring mechanism, and an endplate with a spring mechanism.

FIG. 20 is a top plan view of a tapered inlay and mating endplate.

FIG. 21 is a cross sectional elevation view of an endplate and a convex insert held therein by mating tapered surfaces.

FIGS. 22a, 22b and 23 are cross sectional elevation views of alternative embodiments of locking mechanisms using a pocket and peg received therein.

FIG. 31 is a top perspective view of an inlay and endplate with dovetail shaped guiding strips and grooves.

FIG. 32 is a top perspective view of a modified inlay with easily visible ramps inserted in an endplate.

FIGS. 33 and 34 are respectively a bottom perspective view and a top perspective view of another modified inlay generally similar to that of FIGS. 5 and 3 but with extensions of the ramps which are easily viewed until seated.

FIGS. 35a-b are a bottom and a top perspective view of an inlay which is made more easily removable by the provision of cutouts on the wings and a front end cutout.

FIGS. 36a-b are a bottom and a top perspective view of an inlay similar to that of FIGS. 35a-b above but with a different front end cutout.

FIG. 37 is a top perspective view of an inlay which is made more easily removable by the provision of cutouts in the endplate above the wings of the inlay.

FIG. 50 is a top perspective view of an inlay in an endplate with a side finger locking mechanism.

FIG. 51 is a top perspective view of an inlay in an endplate with another cam locking mechanism.

FIG. 52 is a bottom perspective view of the inlay depicted in FIG. 51 with a top portion of the endplate cutaway to reveal the cams.

FIG. 53 is a top perspective view of an inlay and an endplate with cutouts making removal easier.

FIG. 54 is a top perspective view of the assembled inlay and endplate depicted in FIG. 53.

FIG. 55 is a top perspective view of an inlay in an endplate with another clip locking mechanism.

FIG. 56 is a top perspective view of an inlay in an endplate with a screw operated cam locking mechanism.

FIG. 57 is a top perspective view of an inlay in an endplate with a spring member locking mechanism.

FIG. 58 is a top perspective view of an inlay in an endplate with a removable detent protrusion locking mechanism.

FIG. 59 is a side elevation view of the inlay and detent protrusion depicted in FIG. 58.

FIG. 60 is a bottom perspective view of the detent protrusion being inserted into the inlay of FIG. 58.

FIG. 61 is a top perspective view of an inlay in an endplate with a crimping mechanism.

FIG. 62 is a top perspective view of the inlay crimped into the endplate of FIG. 61.

FIG. 63 is a bottom perspective view of an inlay with a pivoting latch locking mechanism in the open position.

FIG. 64 is a bottom perspective view of an inlay with a pivoting latch locking mechanism in the locking position.

FIG. 65 is a cross sectional top perspective view with the inlay removed but with the pivoting latch locking mechanism of the inlay of FIG. 64 in the closed position in an endplate.

FIG. 68 is a top perspective view of an endplate and lock bar capable of providing a double locking mechanism for an inlay.

FIG. 69 is a bottom plan view of an inlay for use with the endplate depicted in FIG. 68.

FIGS. 70 and 71 are top and bottom perspective views of an inlay with a portion of the guide strip providing a locking mechanism.

FIG. 79 is a bottom perspective view of an inlay with a bottom projection.

FIG. 80 is a top perspective view of an endplate which receives the inlay of FIG. 79 and which is held in place by a screw.

FIG. 81 is a bottom perspective view of an inlay with bottom wings.

FIG. 82 is a top perspective view of an endplate which receives the inlay of FIG. 81 and which is held in place by screws.

FIG. 83 is a bottom perspective view of an inlay and associated locking clip.

FIG. 84 is a top perspective view of an endplate and associated locking clip of FIG. 83 which receives the inlay of FIG. 83 and which is held in place by the locking clip.

DETAILED DESCRIPTION OF THE INVENTION

Figure 1:
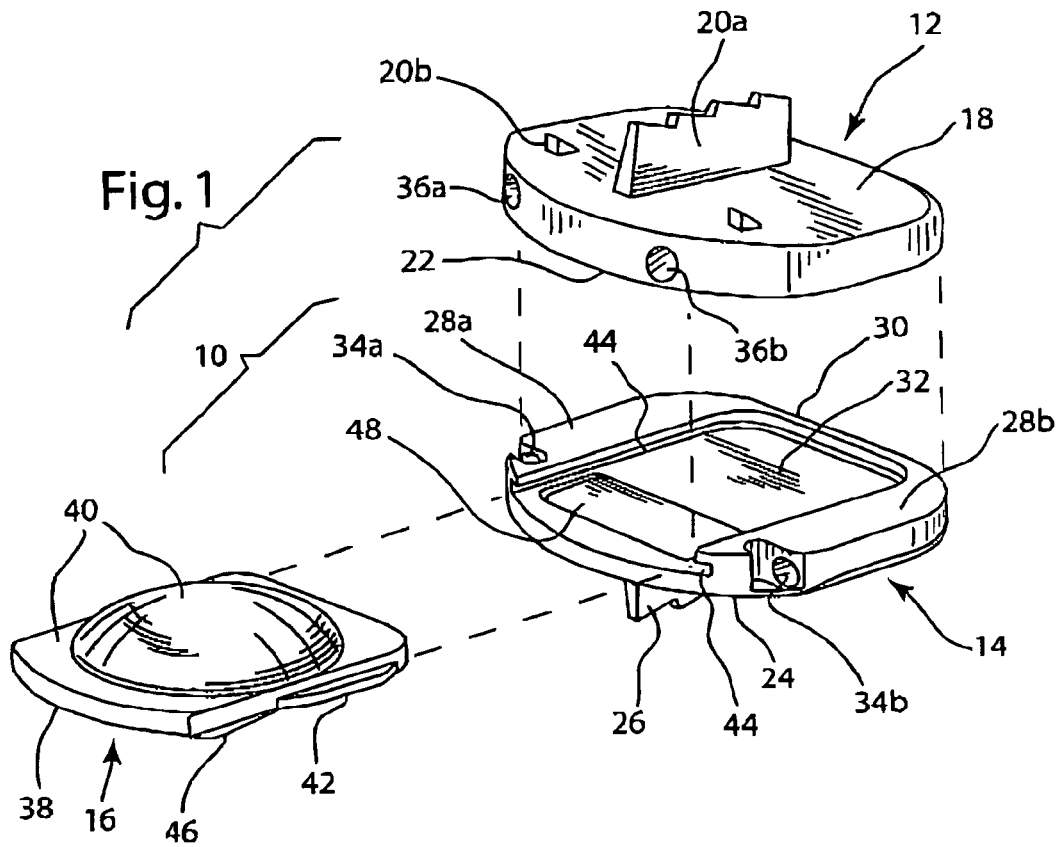
FIG. 1 is a perspective exploded view of an intervertebral implant with an upper part, a lower part, and a pivot insert that can be inserted between them.

With reference now to the drawings where like numerals represent like elements throughout the view, an intervertebral implant 10 of the present invention much like that of the modular implant of U.S. Pat. No. 6,936,071 is shown in the FIGS. 1-2. This modular implant broadly includes three parts, an upper or superior endplate 12, a lower or inferior endplate 14, and a substantially plate-like one-piece pivot inlay 16. The implant 10 is preferably mounted between a superior vertebra and an inferior vertebra and generally replaces an intervertebral disc while preserving limited motion between the superior and inferior vertebra. In plan view, the implant 10, although having rounded corners, is generally rectangular. Modular implant designs are where the plates are typically inserted anterior to posterior into the vertebral body space first followed by insertion of an articulating component (e.g., ProDiscL, Synthes Spine, West Chester, Pa.). A modular design that can be inserted in this manner has a number of advantages; but of course it can also be inserted in two pieces, with the inlay already in the lower endplate if desired. Hereafter, the terms "front" and "back" or "rear" will be used to describe portions of elements in accordance with what direction those elements face when implanted in the body. Thus, for example, the rear of inlay 16 is inserted into the front of endplate 14 when moving from anterior to posterior as shown in FIG. 1.

The upper endplate 12 of implant 10 is preferably flat on its top, creating a support face 18, on which various kinds of protrusions 20a and 20b are disposed which serve the purpose of anchoring the upper endplate 12 in a vertebra that rests, with its end face toward an intervertebral space, on the support face 18. The top of endplate 12 is not limited to being flat and may be shaped and contoured to mate with contoured surfaces of the mating vertebral body or have any desired shape or configuration. The upper endplate 12 is defined by an underside 22 which typically extends substantially parallel to the support face 18 and in which there is a spherical indentation (not shown), which forms a bearing surface for the pivot inlay 16.

The lower endplate 14 of the intervertebral implant 10 on its underside has a preferably flat support face 24 with protrusions 26 (and protrusions like protrusions 20b, but not shown in these views), which correspond to the protrusions 20a and 20b of the support face 18. The support face 24 is not limited to being flat, similar to the above-described top of the upper endplate 12. On the side remote from the support face 24, the thickness of the lower endplate 14 is less in a central region than in an outer region. This outer region of greater thickness has the form of a U, with two parallel legs 28a and 28b, which extend parallel to the short edges of the lower endplate 14, which in cross section is embodied similarly to the upper endplate 12, and with a crosspiece 30 that connects the two legs 28a and 28b on one end. The region enclosed by the legs 28a and 28b and the crosspiece 30 forms a central indentation, pocket or receiving portion 32.

Blind bores 34a and 34b are machined into the two legs 28a and 28b of the lower endplate 14, extending parallel to these legs 28a and 28b from their free ends. Blind bores 36a and 36b, which extend parallel to the blind bores 34a and 34b in the lower endplate 14, are machined into the upper endplate 12, in the vicinity of its side edges. The blind bores 34a, 34b, 36a and 36b serve as receptacles for pin-like extensions of a manipulation instrument (not shown), and thus form engagement elements for this manipulation instrument, which in this way separately engages the upper endplate 12 and the lower endplate 14. With this manipulation instrument, it is possible to introduce the upper endplate 12 and the lower endplate 14 of the intervertebral implant 10 into an intervertebral space; and without inlay 16, this presents a low structural height of the these elements which facilitates this introduction.

Figure 2:
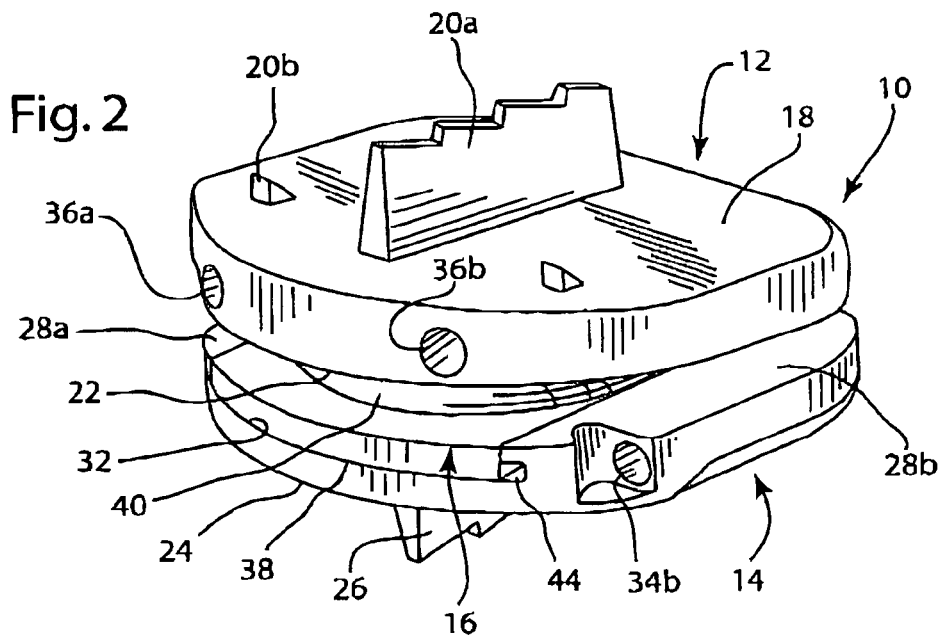
FIG. 2 is a perspective non-exploded view of the implant depicted in FIG. 1.

After the introduction of the upper endplate 12 and lower endplate 14 in this way, the two endplates of the intervertebral implant 10 can be spread apart; that is, their spacing is increased, for instance with the aid of the manipulation instrument that is locking the upper endplate 12 and the lower endplate 14. Thus, in accordance with the method of operation, the upper and lower endplates are first inserted together into the intervertebral space, after which these endplates are separated from each other and the inlay is inserted between them. Thereafter, these endplates are allowed to come together towards each other to bring the intervertebral implant into a working position (FIG. 2).

In this spread open position of the upper endplate 12 and lower endplate 14, it is possible to urge the pivot inlay 16 between the upper endplate 12 and the lower endplate 14. This pivot inlay 16 is constructed essentially in the shape of a plate, which has a flat underside 38 and a spherically upward curved top side 40. The outer dimensions of the pivot inlay 16 correspond to those of the central indentation 32 in the lower endplate 14, so that the pivot inlay 16 can be urged into this indentation, filling it up, specifically from the side toward which the blind bores 34a, 34b, 36a and 36b open. Guide strips or wings 42 on the side edges of the pivot inlay 16 engage corresponding guide grooves or rails 44 in the legs 28a and 28b, so that an insertion guide mechanism for the pivot inlay 16 is formed that assists in securing pivot inlay 16 in the lower endplate 14 after its insertion. The inserted pivot inlay 16, after insertion, fills up the indentation 32 and protrudes with its spherically curved top side 40 upward past the top side of the lower endplate 14; the spherical top side 40 fits in complimentary fashion into the spherically curved indentation (not shown) on the underside of upper endplate 12, so that it forms a ball joint, which enables a certain pivotability of the upper endplate 12 relative to the lower endplate 14 as well known in the art.

The pivot inlay 16 has a detent protrusion 46 on its flat underside 38. Thus, when the pivot inlay 16 is fully inserted into the lower endplate 14, this protrusion locks elastically into a mating detent recess 48 that is located correspondingly in the surface of central indentation 32. As a result, the pivot inlay 16 is also fixed securely in the insertion direction in the indentation 32. In the fully mounted position, the front face of inlay 16 is generally flush with the front face of lower endplate 14 such that a surgeon is preferably able to verify full seating of inlay 16 in lower endplate 14 by running a tool across the surface to verify the edge of inlay 16 does not project past the edge of lower endplate 14.

The upper endplate 12 and lower endplate 14 are preferably made of a physiologically safe metal, such as titanium, while the pivot inlay 16 preferably comprises a likewise physiologically safe plastic material, such as polyethylene. The support faces 18 and 24 can be embodied in an especially bone compatible way; for instance, this surface can be roughened by a coating, so that optimal anchoring to the adjacent bone material is obtained.

The present invention is thus a total disc replacement (TDR) implant to replace the intervertebral disc in the lumbar or cervical spine. The present state-of-the-art has limited material options for the articulating surfaces of the TDRs. Currently the articulating surface is typically comprised of a polyethylene/metal (a CoCr alloy). This is similar to that of the gold standard used in total hip replacements. The present invention permits a surgeon to have several different options for the materials of the articulating surface couple. The options for the couples could be, but are not limited to: titanium alloy, metal-on-improved PE (x-linked PE, compression molded PE, etc.), metal-on-metal, ceramic-on-improved PE, ceramic-on-ceramic, metal-on-ceramic, metal matrix composite (MMC) and other couples that preferably produce little relative wear. Coatings or films known in the art to reduce wear and/or corrosion of metal or other components could also be used as desired.

Referring to FIGS. 3-7 a modular inlay 50, which could be used in place of the inlay 16 noted above to accommodate different material combinations, is shown. The inlay 50 includes a proximal end 52c, a distal end 52d, an engaging surface 52a and an exposed surface 52b. The inlay 50 also includes a base 52 with a through hole 54 therein designed to accept a first insert 56. The first insert 56 is adapted to be mounted to the inlay 50 and has a first articulating surface 56a. The features designed to accept the insert 56 may be any shape or design best suited for attachment to the inlay 50. With this design of the inlay 50, the insert 56 is a separate component that is assembled to the inlay 50. As a result, the articulating surface 56a of the insert 56 can be made from any desired material, such as (but are not limited to): ceramics, metals, polymers or other material types that are known in the art to be good articulating couple materials. The insert 56 is attached to the modular inlay base 52 (or a superior endplate if desired instead) using any familiar attachment method known in the art such as: a shrink fit, a press fit, a biocompatible adhesive, etc. The insert 56 is preferably mounted to the insert 56 in the through hole 54 during the manufacturing process by the manufacturer, but is not so limited and may be designed such that the end user is able to mount the insert 56 to the inlay 50.

The modular inlay 50 is also preferably associated with a second insert 57, which preferably has the same shape and size as the first insert 56. The second insert 57 is also preferably adapted to be mounted to the inlay 50 and has a second articulating surface 57a. The first articulating surface 56a is preferably constructed of a first material and the second articulating surface 57a is preferably constructed of a second material. The first and second materials are preferably different from each other and may be comprised of nearly any material that provides acceptable wear resistance and biocompatibility when implanted between the superior and inferior vertebrae. For example, the first material may be comprised of a metal material and the second material may be comprised of a ceramic material. The inlay 50 and combination of inserts 56, 57, thereby provide adaptability for a surgeon to implant the intervertebral implant 10 having a preferred combination of articulating surfaces, depending upon the surgeon preferences or specific surgical situation. The second insert 57 is also preferably mounted in the inlay 56 by the manufacturer, but is not so limited and may be mounted to the inlay 56 by the end user.

The inlay 50 with at least one of the inserts 56, 57 in place is designed to be inserted into and mate with a first (inferior or superior if desired) endplate 58 of the TDR as shown in FIG. 7. The first endplate 58 includes a front end 58a and a rear end 58c. The first endplate 58 also includes an inner surface 58c and an outer surface that engages the superior or inferior vertebra to secure the implant 10 to the spine. The modular inlay 50 mates with a corresponding receiving portion 60 in endplate 58 and is securely attached to endplate 58 upon full insertion. This is accomplished by use of rails 62 in endplate 58 and corresponding wings 64 on lateral edges of inlay 50 to engage with mating receiving portion 60 of endplate 58. It will be noted that wings 64 preferably extend along only a part of the lateral edge of inlay 50, but may extend along the entire edge of the inlay or may be interrupted along the edge of the inlay 50.

In order to securely lock modular inlay 50 into endplate 58, inlay 50 includes a taper lock mechanism. This lock mechanism includes inferior lateral ramps 66 as best shown in FIGS. 5 and 6 and which act like springs or resilient catches. In operation, lateral ramps 66 deflect slightly upon insertion into endplate 58 as they contact the rear edge of receiving portion 60; and then when inlay 50 is fully inserted into receiving portion 60, they spring back into mating cutouts 68 provided in receiving portion 60 to retain inlay 50 securely within endplate 58. If desired, cutouts 68 could instead be a single lateral cutout rather than two separate cutouts.

The Inlay 50 and/or the mating endplate 58 may have a special coating or process to aid in the reduction of wear and corrosion between the two mating surfaces (or separate element if so desired) of the (superior or inferior) endplate. As with implant 10 described above, modular inlay 50 is held with the instruments necessary to insert inlay 50 into inferior endplate 58 based on the surgical procedure being used. The inlay 50 is preferably made from a titanium alloy, while insert 56 is made of any desired material, preferably polyethylene, metal or ceramic.

While the embodiment of implant 10 depicted above included only a single inferior modular inlay 50, it would also be possible to make use of a modular inferior inlay 70 similar to inlay 50 with a lower endplate 72 and a modular superior inlay 74 with an upper endplate 76 as depicted in FIG. 8 to create a TDR 78. In this embodiment, it will be noted that superior inlay 74 includes an insert 80 with a concavity to match the convexity of inferior insert 82. In addition, unlike inlay 50, both inlays 70 and 74 have a single ramp 84 which extends from one side to the other of the inlay as shown best by inlay 74 shown in FIG. 9. Each ramp 84 also includes a central cutaway portion coextensive with the through hole (for accepting the insert), so that each ramp 84 is attached to the associated inlay 70, 74 at each side but not in the middle at the location of the cutaway portion (not shown). In order to lock each inlay 70, 74 in place with ramps 84, both endplates 72 and 76 include a respective cutout 86 (shown only in superior endplate 76) shaped to receive the associated ramp 84 when the associated inlay 70 or 74 is fully inserted therein. Ramp 84 and inlays 70, 74 are not limited to such constructions, and may be configured and constructed to have nearly any shape or size that permits operation of the implant 10 in the described manner.

Depicted in FIG. 10 is a modified inlay 88 similar to inlay 70 (or 74), but with a spring mechanism 90 at the posterior end thereof formed by two arms 92. Spring mechanism 90 is designed to be compressed when inlay 88 is fully inserted in lower endplate 72, to accommodate for tolerance dimensions and the like of inlay 88 and endplate 72 whereby a secure fit is provided between the two preferably without any play or micromotion. Another modified inlay 88' similar to inlay 88 is depicted in FIG. 11a. Inlay 88' has a spring mechanism formed by two coil springs 92' as shown.

Yet another modified inlay 88" similar to inlay 88 is depicted in FIG. 11b. Inlay 88" has a spring mechanism formed by a short extension of the longitudinal end (relative to a no-spring inlay) and the presence of a cavity 92" behind this end into which the end can be resiliently deflected when engaged with a cross piece of the endplate as inlay 88" is fully received in the receiving portion of the endplate. Additionally if desired, or as an alternative to the use of cavity 92" on inlay 88", a cross piece 89 of an endplate 91 can be extended inwardly slightly, and a cavity 93 provided therein as shown to provide a (or another) spring mechanism. When the rearward end of inlay 88" contacts cross piece 89 of endplate 91, cross piece 89 will be deflected inward towards cavity 93 as inlay 88" is fully received therein, just as the end of inlay 88" with cavity 92" will likewise be deflected if present.

Figure 12:
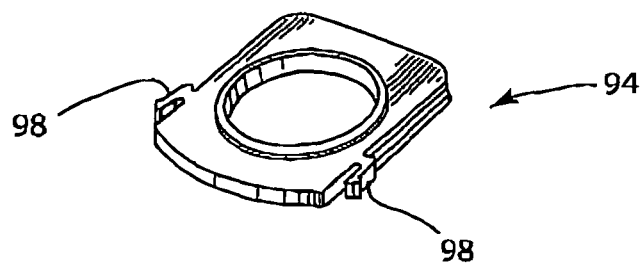
FIG. 12 is a top perspective view of an alternative inlay with fingers forming a lateral locking mechanism.
Figure 13:
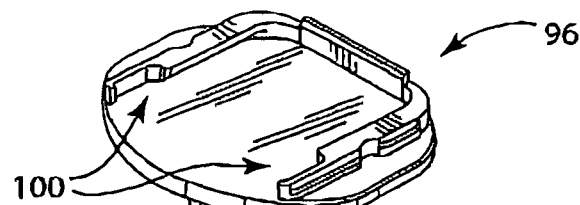
FIG. 13 is a top perspective view of an alternative endplate with cutouts for the fingers of the inlay of FIG. 12.
Figure 14:
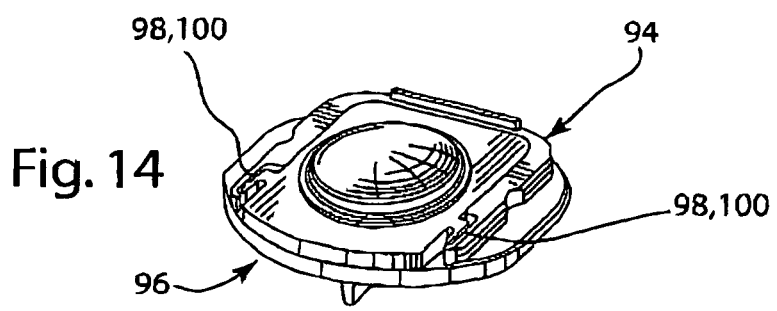
FIG. 14 is a top perspective view of the assembled inlay and endplate of FIGS. 12-13.

Depicted in FIGS. 12-14 is an alternative embodiment including an inlay 94 similar to inlay 50 but with a different mechanism for locking inlay 94 in a lower (or upper) endplate 96 which is similar to endplate 58. In this embodiment, each lateral edge of the inlay 94 is provided with a lateral anterior finger 98 which acts as a lateral spring (and in place of the ramps 66 in the inlay 50). Endplate 96 is provided with mating lateral cutouts 100 in the lateral edges thereof. Thus, when inlay 94 is fully inserted in endplate 96, fingers 98 act as biased springs that deflect slightly upon initial insertion into cutouts 100, and which then spring back to engage within cutouts 100 to provide a secure fit therein and a visual indication for the surgeon.

Figure 15:
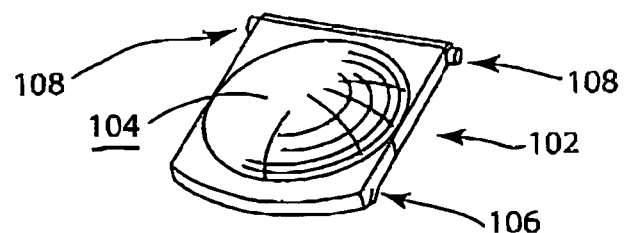
FIG. 15 is a top perspective view of an alternative inlay with lateral locking pins.
Figure 16:
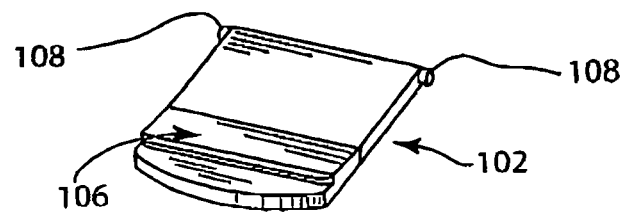
FIG. 16 is bottom perspective view of the alternative inlay depicted in FIG. 15.
Figure 17:
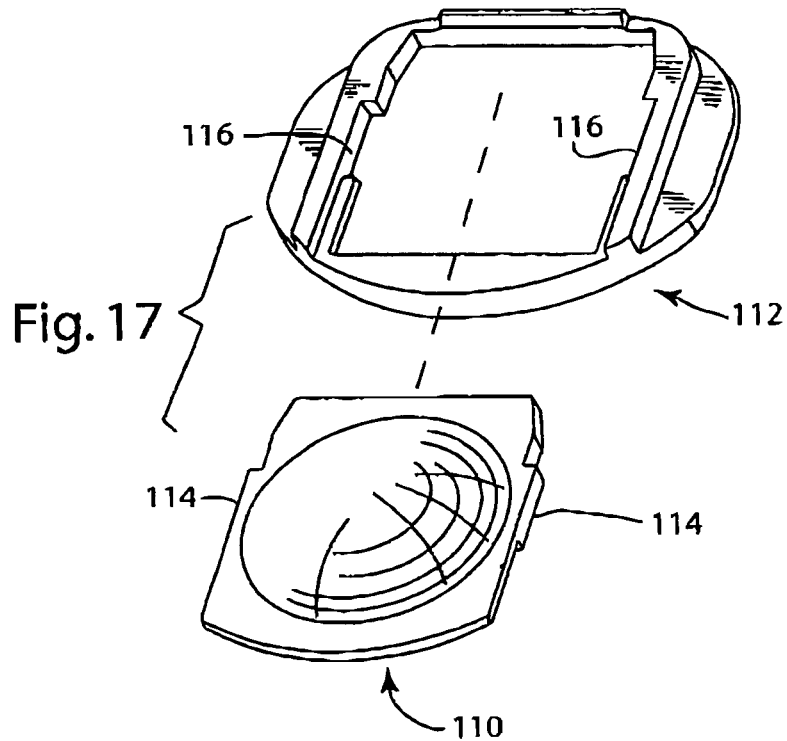
FIG. 17 a top perspective view of an inlay and mating endplate with a drop-in locking mechanism.

Depicted in FIGS. 15-16 is an alternative embodiment of an inlay 102 which is broadly similar to inlay 74 depicted in FIGS. 8-9. Inlay 102 has an integral articulating surface 104, and thus no through hole like inlay 74 to accept a separate insert (though that could be provided if desired). With this design, inlay 102 includes a ramp 106 extending all of the way between the lateral sides thereof as shown. Inlay 102 also includes lateral pins 108 which are used to guide inlay 102 when it is inserted in an endplate like endplate 72 discussed above and having guide grooves 44 like endplate 14 (whereas inlay 74 included wings for guidance which were like wings or guide strips 42 discussed above). By use of pins 108 at the rearward end, inlay 102 can be inserted not only in an orientation which is parallel to the receiving endplate as shown in FIG. 8 for inlay 70, but it can be tilted or rotated upwards somewhat so as to be oriented as may be desired during insertion. When inlay 102 is fully inserted, inlay 102 will drop into the correct position within the corresponding receiving portion of the endplate (not shown, but similar to endplate 14 shown in FIG. 1), where it will then be held in place during use by engagement with the superior endplate. Inlay 102 may also include a separate locking mechanism or taper to further secure inlay 102 to the endplate. Pins 108 thus serve as guide features during insertion, and also prevent inlay 102 from disengaging from the endplate during and after insertion. While pins 108 would typically be cylindrical in shape to allow rotation, they could be hemispherical in shape or any other shape suitable to allow insertion and serve as a guidance feature.

Where it is desired not to use guiding wings and rails or the like, an inlay 110 as depicted in FIG. 17 can be used. Thus upon insertion, inlay 110 slides across an inferior implant endplate 112 and then drops into place to engage with implant endplate 112 (so that is then permanently locked in place once engagement with the adjacent endplate is made). This sliding is accomplished by providing inlay 110 with lateral wings 114 along a portion (or all) of each lateral side to aid in the sliding or gliding insertion. The Wings 114 drop into place in corresponding mating cutouts 116 in the lateral sides of the endplate 112 when longitudinal insertion is completed, thereby visually indicating complete insertion of the inlay 110 in the endplate 112. The wings 114 could include various shapes besides rectangular (such as pyramidrical, etc.), so long as the inlay 110 mates with the inferior endplate 112. In addition, the inlay 110 itself could include tapered features to provide for a secure press fit when it drops into the receiving portion of the endplate 112. It is expected that the inlay 110 would be implanted from an anterior approach, but it is not so limited—especially as other approaches may be appropriate with slight modifications to the implant features (i.e., oblique, anteriolateral, posterior, etc.). The use of the inlay 110 may also make it possible to remove the inlay 110 from various approaches to aid in revisions from an anterior, anteriolateral, oblique approach.

Figure 18:
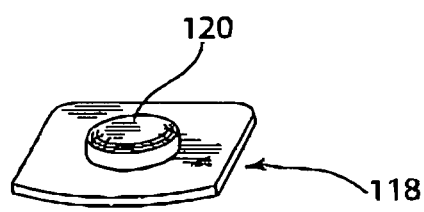
FIG. 18 is a bottom perspective view of a drop-in inlay with a protrusion locking mechanism.
Figure 19:
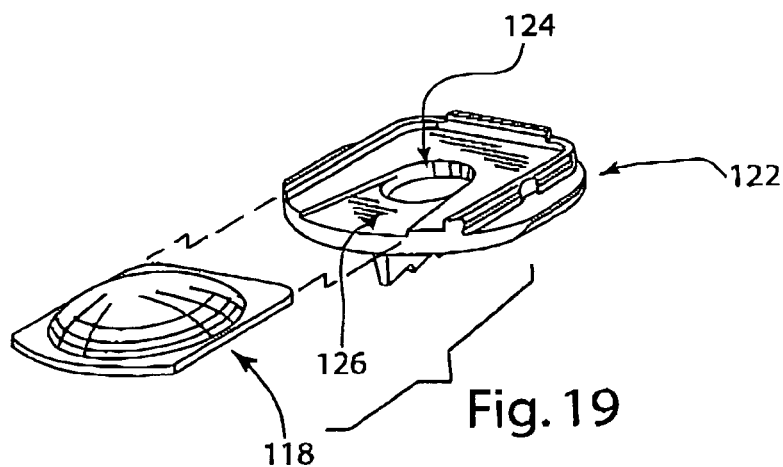
FIG. 19 is a top perspective view of the inlay in FIG. 18 and a mating endplate.

An alternative to the drop-in inlay 110 discussed above is an inlay 118 depicted in FIGS. 18-19. Inlay 118 includes a button or other shaped protrusion 120 on the bottom face, which mates with endplate 122. Endplate 122 then includes a mating pocket 124 in the receiving portion into which protrusion 120 is suitably received as by providing protrusion 120 and pocket 124 with a slight (e.g., 5°) mating taper. Preferably, the receiving portion of endplate 122 also includes a guide slot 126 along which protrusion 120 will slide and be guided into a resting position in pocket 124; and at the same time, the remainder of inlay 118 will be snugly received in the receiving portion of endplate 122. Once protrusion 120 drops into pocket 124 and hence inlay 118 into endplate 122, inlay 118 will then be generally prevented from lateral movement. However, if desired, play could be provided between protrusion 120 and pocket 124, as well as between the sides of inlay 118 and the receiving portion of endplate 122, so that translational movement of inlay 118 in endplate 122 would be allowed to some degree in one (x or y) direction or in a plane (both x and y). It will also be appreciated that protrusion 120 could be ramp-shaped with the thickest or highest part at the front so as to more easily be introduced into endplate 122 and to ride along with less friction as a smaller surface area would engage the receiving portion of endplate 122.

One embodiment of a taper lock mechanism was depicted above in FIG. 17, but not described. A similar taper lock mechanism is depicted in FIG. 20, which shows a distally tapered inlay 130 which is received in a matingly tapered pocket or recess 132 of an endplate 134 to securely lock inlay 130 into the endplate 134. The recess 132 includes a first tapered surface 132a formed therein. The endplate 134 includes a front end 134a, a rear end 134b, an inner surface 134c and an outer surface for engaging the superior or inferior vertebra in a mounted position. The inlay 130 has a proximal end 130c, a distal end 130d, an exposed surface 130b and an engaging surface that is supported by the inner surface 134c in the mounted position. The inlay 130 includes a second tapered surface 133 that mates with the first tapered surface 132a to secure the inlay 130 to the endplate 134 through an interference fit between the inlay 130 and the endplate 134. Such a locking taper is designed to preferably minimize or substantially limit any micro-motion between the two elements, and to limit the potential for frontside wear debris. It will be appreciated that the taper could also be in different planes/faces of the components and/or in different locations on the components.

The inlay 130 preferably includes a resilient ramp 131 secured to the engaging surface and a cavity 135 is preferably formed in the recess 132. The resilient ramp 131 is positioned in the cavity 135 in the mounted position. The first and second tapered surfaces 132a, 133 facilitate engagement of the resilient ramp 131 with the cavity 135 to limit micromotion between the inlay 130 and the endplate 134. Preferably, when the intervertebral implant 10 is implanted in a patient, the loading of the spine and the implant 10 tends to urge the resilient ramp 131 into engagement with the cavity 135 away from the rear end 134b.

Use of a convex insert assembled directly to an inferior (or superior) plate intra-operatively is also possible. For example, depicted in FIG. 21 is an endplate 136 which would have already been positioned in an intervertebral space with an opposite (superior or inferior) endplate positioned adjacent thereto (not shown). The endplate 136 is provided with a tapered pocket 138 including a first tapered surface 138a. A convex insert 140 with a tapered end 142 defining a second tapered surface 142*a* is then moved over and dropped into the pocket 138 to provide secure engagement of the insert 140 to the endplate 136, especially in use when the superior endplate will bear down and engage the articulating surface of the insert 140. Alternatively, the insert 140 could also be assembled to the endplate 136 in the operating room, and the whole implant assembly inserted as one piece into the intervertebral space if so desired.

Depicted in FIG. 22*a* is an alternative mechanism for locking a modular inlay 144 in place on an endplate 146 and for preferably limiting any micromotion between these two components. In this embodiment, inlay 144 includes a tapered pocket 148 which mates with a tapered peg 150 provided on endplate 146. The positions of pocket 148 and peg 150 could also be reversed, as shown in FIG. 22*b*, where an inlay 144' is provided with a tapered peg 150' which mates with a tapered pocket 148' provided in an endplate 146'. The peg/pocket features could be provided on either the anterior or posterior side of the implant. However, having the peg/pocket features on the anterior side is preferred since the inlay could then slide over the inferior plate with the extending peg only engaging and then seating at the end of the movement when the inlay is fully inserted into the endplate. It will also be appreciated that instead of tapered peg/pocket features, the features could be a tapered (lateral) ridge and groove as well. If desired and as shown in FIG. 23, where a peg 150" is provided on the rearward end, endplate 146" could be provided with teeth 147 therealong so that peg 150" would ratchet along teeth 147 until it dropped into pocket 148" providing secure engagement, and with the taper, minimizing micromotion.

Figure 24:
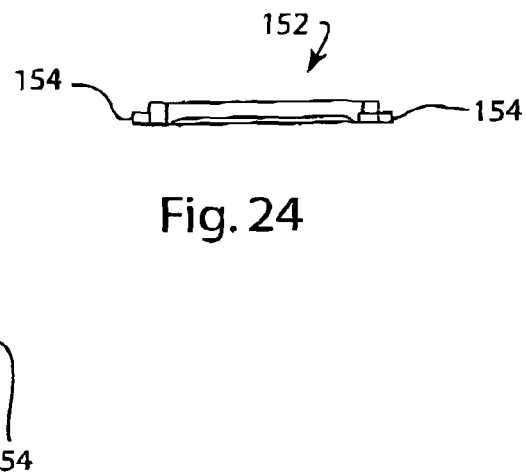
FIG. 24 is a rear elevation view of an inlay with laterally directed locking fins.
Figure 25:
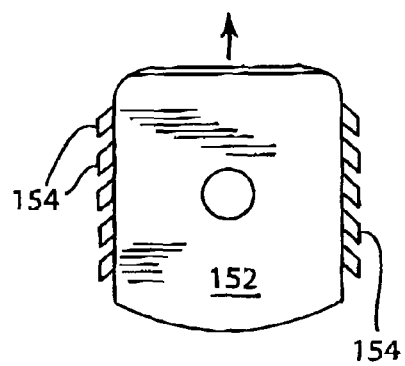
FIG. 25 is a bottom plan view of the inlay depicted in FIG. 24.
Figure 26A:
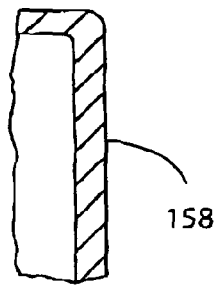
FIGS. 26a and 26b are first and second embodiments of a partial horizontal cross sectional view through a part of a receiving portion of an endplate in which the fins of the inlay depicted in FIG. 25 are received.
Figure 26B:
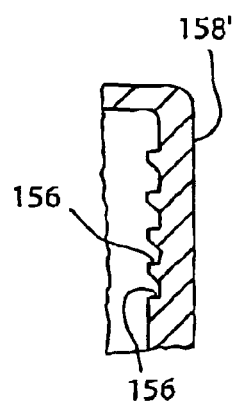
Figure 27:
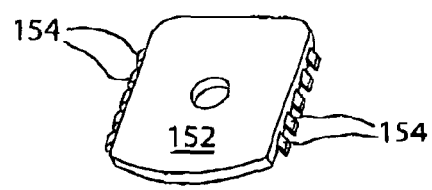
FIG. 27 is a top perspective view of the inlay depicted in FIG. 24.

Depicted in FIG. 24 which is a rear view, in FIG. 25 which is a bottom view and in FIG. 27 which is a top perspective view is an inlay 152 having a plurality of laterally extending, frontwardly (or backwardly, relative to the direction of insertion shown by the arrow in FIG. 25) angled fins 154. Fins 154 provide an interference fit with the guide rails of an associated inferior (or superior) endplate such as shown in FIG. 26*b* but similar to any of the above in order to lock inlay 152 securely in place. Fins 154 deflect frontwardly slightly upon insertion of inlay 152, allowing inlay 152 to be assembled under only a moderate amount of force. Once assembled, inlay 152 resists expulsion by the frontwardly angled direction of fins 154 engaging the side surface of the endplate. With a frontward's force, fins 154 tend to deflect slightly outward, essentially expanding the width of inlay 152 so as to resist expulsion from the endplate. The engaged side surfaces of the guiding grooves of the endplate may be smooth as typically provided in the above embodiments as shown by side 158 in FIG. 26*a*, or the sides may have features that increase the friction and/or locking potential of inlay 152 such as by the provision of a small step or steps 156 as shown in FIG. 26*b* on side 158' of the guiding grooves of an endplate (not otherwise shown). Alternative to steps 156, the endplate may include other types or designs of cutouts, protrusions, roughened portions, or the like.

With inlay 152, it will be noted that the center of rotation of the convex articulating insert (not shown, but it would be attached in the center hole) could be positioned in the longitudinal location as desired by the surgeon. Since inlay 152 allows only a one-way insertion, it does not necessarily have to be inserted until inlay 152 reaches the rear wall of the endplate. Rather, the surgeon can insert inlay 152 as far as desired, to position the center of rotation of the convex insert in the ideal location as determined intra-operatively. Further insertion of inlay 152 should not be a problem since most of the forces on inlay 152 will be in the removal direction only.

Besides allowing for longitudinal insertion, it would also be possible in a not shown embodiment to provide an inlay for dropping into place in the associated receiving portion of an endplate. In accordance with this embodiment, the side fins extend away from the direction of insertion (the dropping in direction), so the fins would likewise resist movement of the inlay out of the associated endplate.

Figure 28:
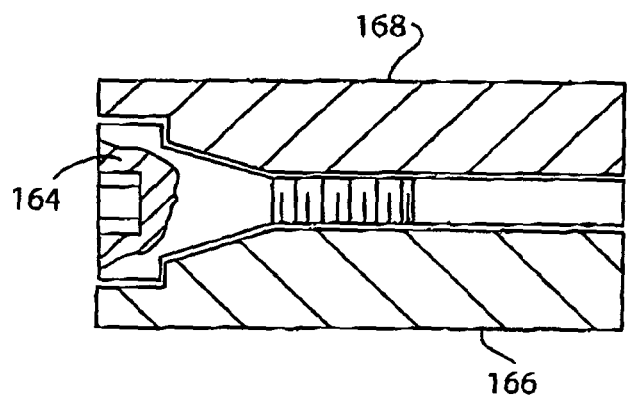
FIG. 28 is a vertical cross sectional view of an endplate and a matching inlay locked together by a longitudinally oriented screw.

In lieu of, or in addition to locking mechanisms discussed above, another locking mechanism is depicted in FIG. 28. This locking mechanism is a pin or screw 164 which is received between an endplate 166 and an inlay 168 to provide secure engagement therebetween. The screw threads of screw 164 thus engage opposed portions of endplate 166 and inlay 168, preferably preventing micromotion therebetween in the direction of the screw (and laterally or left-right as well). After insertion of inlay 168 into endplate 166, screw 164 is simply inserted by the surgeon (either additional to another locking mechanism, or as the only locking mechanism). Besides a screw, additional locking components which could be used for this purpose include a pin, a cammed pin, or some other such component. It will be noted that the head of screw 164 after full insertion is preferably located in recesses provided in endplate 166 and inlay 168.

Figure 29:
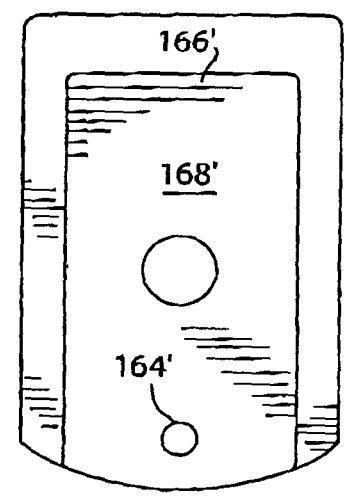
FIG. 29 is a top plan view of an endplate and a matching inlay locked together by a vertically directed screw.

Depicted in FIG. 29 is another locking mechanism using a screw 164'. In this embodiment, screw 164' is screwed down through inlay 168' and then into endplate 166'. By engaging both inlay 168' and endplate 166', the two are thus securely engaged and micromotion therebetween eliminated or minimized.

Figure 30:
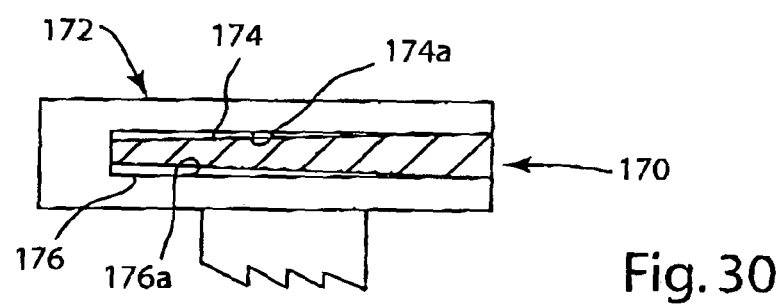
FIG. 30 is a vertical cross sectional view of a modified inlay and endplate generally similar to that of FIG. 3 with a tapering locking mechanism on the inlay.

Depicted in FIG. 30 is another locking mechanism which can be used to provide secure engagement between an inlay 170 (only a portion of which is shown) and an endplate 172. In this embodiment, inlay 170 includes a lateral guide strip or fin 174 on each lateral side which engages a respective guide groove 176 provided in endplate 172 (similar to guide strips 42 and guide grooves 44 noted above in FIGS. 1-2). The fin 174 preferably includes a second tapered surface 174*a* and the groove 176 preferably includes a first tapered surface 176*a* that mate with each other in the mounted position. However, it will be noted that guide strip 174 is tapered from thickest to thinnest in the insertion direction. Thus, as inlay 170 is inserted into endplate 172, guide strips 174 eventually become wedged in guide grooves 176 to securely lock inlay 170 to endplate 172 and generally prevent micromotion. While the taper has been depicted on guide strips 174, it will be appreciated that as an alternative, each guide groove could end in a taper in which an un-tapered guide strip could then be received to provide a similar locking mechanism.

Instead of using rectangular wings or guide strips 42, 64, etc., it would also be possible to use guide strips of other shapes such as a dovetail shaped guide strip 178 provided on an inlay 180 as depicted in FIG. 31. In order to receive both dovetail shaped guide strips 178, matingly shaped guide grooves 182 are preferably provided on endplate 184, as also shown.

In FIGS. 3-7 above, an inlay 50 with ramps 66 was described which was received in an endplate 58 with a corresponding cutout 68 for ramps 66. With this type of design, it is sometimes not easy to tell exactly when ramps 66 are fully engaged in cutouts 68 when inlay 50 is inserted in endplate 58 located in an intervertebral space. In order to provide a visual indication of the proper and full seating of ramps in cutouts, there is depicted in FIGS. 32*a-b* a modified inlay 186 with ramps 188. The inlay 186 is received in an endplate 58' (generally similar to endplate 58 described above) having corresponding cutouts 68' for ramps 188. The endplate 58' includes a front end 58a, a rear end 58b, an inner surface 58c and an outer surface for engaging the superior or inferior vertebra in a mounted position. A recess 59 is formed in the inner surface 58c and the endplate 58 includes a front surface 58d. The inlay 186 has a proximal end 186a, a distal end 186b, an engaging surface and an exposed surface 186c. The engaging surface is supported by the inner surface 58c and the inlay 186 is positioned in the recess 59 in the mounted position. The resilient ramp 188 extends from the engaging surface and is positioned in the cutout 68' in the mounted position. The resilient ramp 188 has a root end 188a and a terminal end 188b. The terminal end 188b is visible to a user, preferably a surgeon, such that the exposed surface does not extend over the terminal end 188b in the mounted position.

In particular, it will be noted that ramps 188 extend frontwardly behind the remaining portion of inlay 186, and on either side of tab 190 defining a laterally reduced frontward portion of inlay 186. Thus, as evident from FIG. 32b, when inlay 186 is fully longitudinally received within the receiving portion of endplate 58', that is when ramps 188 are fully received in cutouts 68', the position of ramps 188 in cutouts 68' on either side of tab 190 is visible to the surgeon making the insertion when viewed longitudinally. In particular, the surgeon will be able to see ramps 188 when they are raised up and riding along the receiving portion of endplate 58', and then when ramps 188 drop into cutouts 68' (and change position)—which should also be accompanied by a small audible sound and tactile vibration which will also aid the surgeon in knowing that full insertion and locking has occurred. The surgeon can then be assured that inlay 186 is thus fully inserted into endplate 58'.

Another embodiment of an inlay 192 which allows the surgeon to see if it has been fully inserted in an endplate 58' is shown in FIGS. 33-34. In this embodiment, inlay 192 includes extensions or a terminal end 194 protruding from the frontward ends of ramps 196, wherein a root end 196a of the ramp 196 is secured to an engaging surface of the inlay 192. When ramps 196 are in their engaged position in endplate 58', the resting position shown in FIGS. 33-34, the upper (for an inferior insert) surface 198 of extensions 194 are substantially coplanar with the upper surface of inlay 192 as best shown in FIG. 34. However, when inlay 192 is being inserted longitudinally into endplate 58', the ramps 196 are pushed upwards as they ride along the receiving portion of endplate 58'. As the ramps 196 are raised, the upper surfaces 198 are similarly raised and jut above the surrounding surface of the inlay 192. It is only when the ramps 196 spring back down into the cutouts of the endplate 58' that the upper surfaces 198 return to essentially their rest position where they are generally coplanar with the upper surface of the inlay 192. This dropping of the upper surfaces 198 is easy for the surgeon to see as the inlay 192 is inserted, and signals that the inlay 192 is fully inserted such that the ramps 196 have properly dropped into the cutouts of the endplate 58' to securely lock the inlay 192 in place. It will be appreciated that a number of different variations in the geometry of the ramps 196 and the upper surfaces 198 could be provided to create the same concept of having the two lateral ramps 196 have portions which deflect or are viewable above the inferior plate surface during insertion. Alternatively, the ramp 196 could be viewable only when insertion is complete, but this is considered less desirable in most circumstances. In this embodiment, the inlay 192 includes a width W1 at its proximal end 192a that is reduced when compared to a width W2 of the inlay 192 at its distal end 192b.

After insertion, it is sometimes desired to replace an inlay previously inserted into an endplate, or to replace the entire endplate-inlay assembly which may be made easier by first removing the inlay. Typically, removal of the inlay is accomplished with a "lift and pop-out" maneuver. In this procedure, an osteotome or some other like instrument is inserted underneath the inlay, and the osteotome is then rotated to lift/pry the inlay, resulting in bending or breaking of the side tab of the inlay or whatever locking feature of the endplate is provided so that the inlay is no longer attached to the endplate and hence can be easily removed. In order to better accommodate such a removal action, an inlay 200 is provided as shown in FIGS. 35a-b. Compared to other inlays as described above, inlay 200 has guide strips or wings 202 which have a reduced thickness portion 204 therealong as shown. As a result of reduced thickness portions 204, wings 202 will have a lower yield strength, and in particular will more easily allow bending and deflection. If desired, wings 202 could also have a notch or score machined into them to allow them to flex even more easily, for example, the reduced thickness portion 204 is similar to a notch or score that permits flexing of the wings 202.

Another way to make it easier to remove inlay 200 is also shown in FIG. 35a-b. Compared to other inlays, inlay 200 includes reduced portions or cutouts 210 on either side of the front end. Cutouts 210 are designed to facilitate the introduction of an osteotome or other instrument thereunder, so that cutout 210 provides a window to allow for introduction of the osteotome or other instrument to effect the prying required of inlay 200 out of the associated endplate. Instead of a complete cutout opening, there could also be a slight chamfer or the like to allow for getting an osteotome in between inlay 200 and the inferior plate. Cutouts 210 can also be used separately or in conjunction with reduced thickness portions 204 as described above. Another inlay 200' similar to inlay 200 is depicted in FIGS. 36a-b and has the same elements identified with the same numerals. Instead of cutouts 210, inlay 200' includes a single, central cutout 210' to make it easy to pry inlay 200' out of the associated endplate.

Still another way simplify removal of an inlay 214 is shown in FIG. 37 with an associated endplate 212. As shown, endplate 212 includes small window cutouts 216 formed in the guiding grooves or rails 218 beneath which inlay 214 is trapped. Cutouts 216 facilitate easier removal, preferably via prying up of inlay 214. Preferably, inlay 214 also includes lateral tabs or wings 220 positioned when fully inserted approximately midway along the length of inlay 214 and underneath of cutouts 216. These tabs 220 would then lift vertically out through cutouts 216 to permit removal of inlay 214 from endplate 212.

Figure 38:
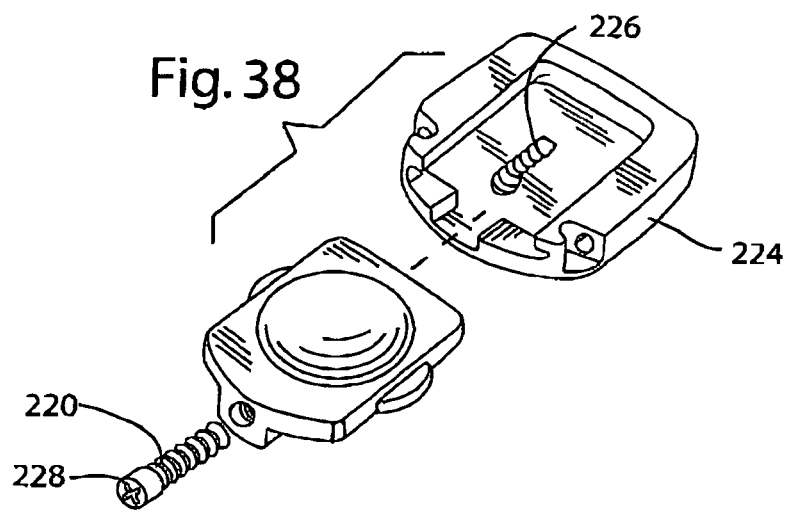
FIG. 38 is a top perspective view of an inlay and endplate with another screw locking mechanism.
Figure 39:
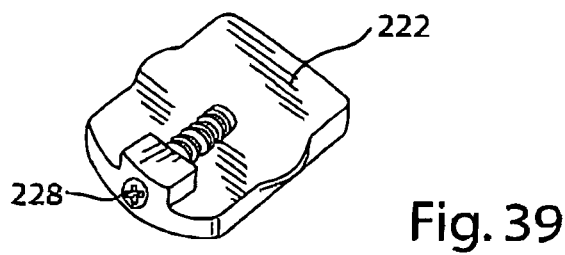
FIG. 39 is a bottom perspective view of the inlay depicted in FIG. 38.

Besides the various mechanisms to lock an insert into an inlay as discussed above, there are a variety of other mechanisms or variations which could also be used. For example, depicted in FIGS. 38-39 is another variation of a screw 220 which is used to lock an inlay 222 and an endplate 224 against movement similar to that shown in FIG. 28 discussed above. In this embodiment, it will be appreciated that screw 220 is initially received in the front end of inlay 222, which has been thickened as shown for this purpose, and thereafter the screw threads thereof engage the facing surfaces of inlay 222 and endplate 224 which have been provided with receiving thread portions 226 (shown best in endplate 224 in FIG. 38) for this purpose. It will also be appreciated that a head 228 of screw 220 is preferably flush (or slightly recessed if desired) in inlay 222 when fully inserted as shown in FIG. 39.

Figure 40:
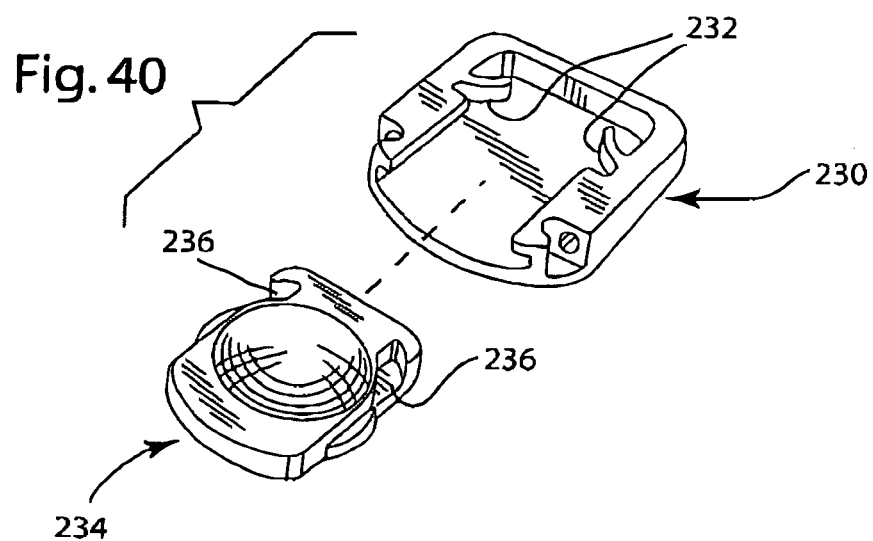
FIG. 40 is an exploded top perspective view of an inlay and an endplate with rear locking fingers.

Another modification to an above noted embodiment in FIGS. 12-13 is shown in FIG. 40. Rather than having fingers on an inlay and cutouts in an endplate as is discussed and shown in FIGS. 12-13, an endplate 230 is provided with fingers 232 extending into the receiving portion, and an inlay 234 is provided with cutouts 236 to receive fingers 232 upon full insertion of inlay 234. To better ease and then lock fingers 232 in place, it will be appreciated that fingers 232 are angled in the insertion (rearward) direction and will resiliently give as/until cutouts 236 are positioned to receive them. It will also be noted that fingers 232 and cutouts 236 are provided at the rear, rather than in the front as with the embodiment shown in FIGS. 12-13.

Figure 41:
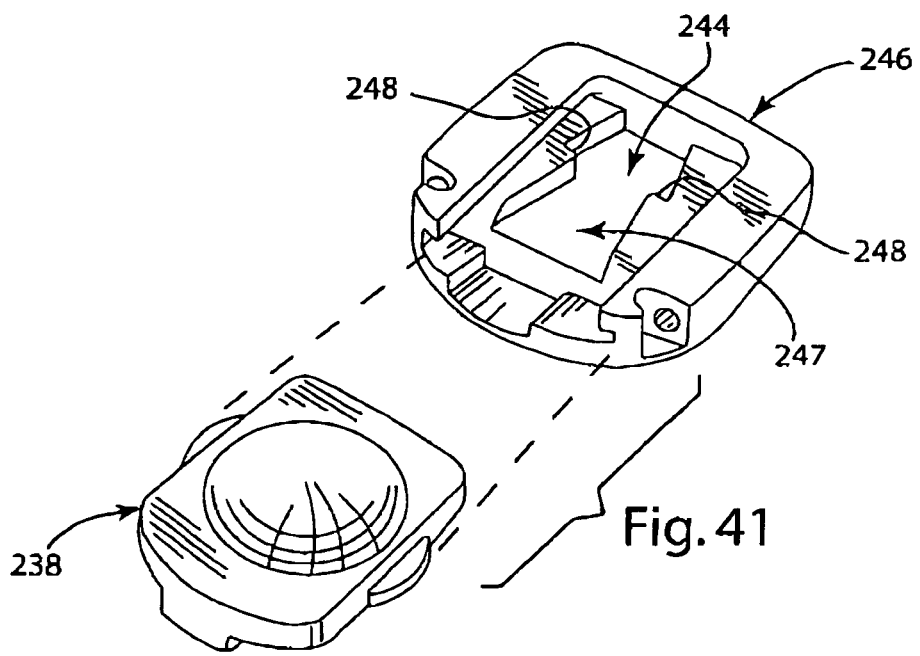
FIG. 41 is an exploded top perspective view of an inlay and endplate with a clip/catch locking mechanism.
Figure 42:
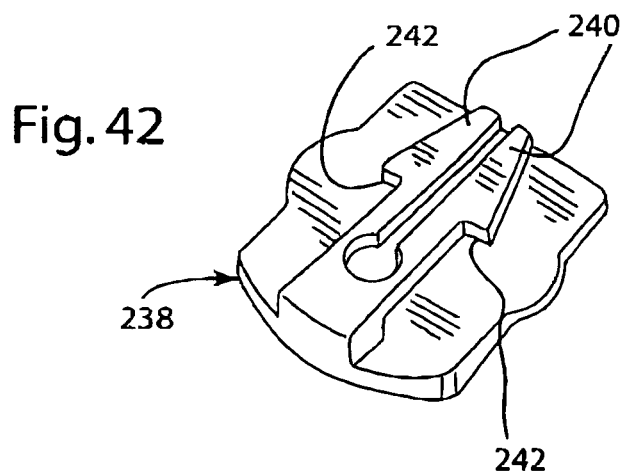
FIG. 42 is a bottom perspective view of the inlay depicted in FIG. 41.

Another spring-actuated locking mechanism is depicted in FIGS. 41-42. In this embodiment, an inlay 238 is provided on its underside with integral resilient arms 240 having catch shoulders 242 and hence forming a clip-like member. Arms 240 are received in a mating channel 244 of endplate 246, thereby forming a catch. In operation, arms 240 are initially pushed resiliently together as they enter a guiding portion 247 of channel 244, but eventually arms 240 spring outwards and shoulders 242 are captured by edges 248 of channel 244.

Figure 43:
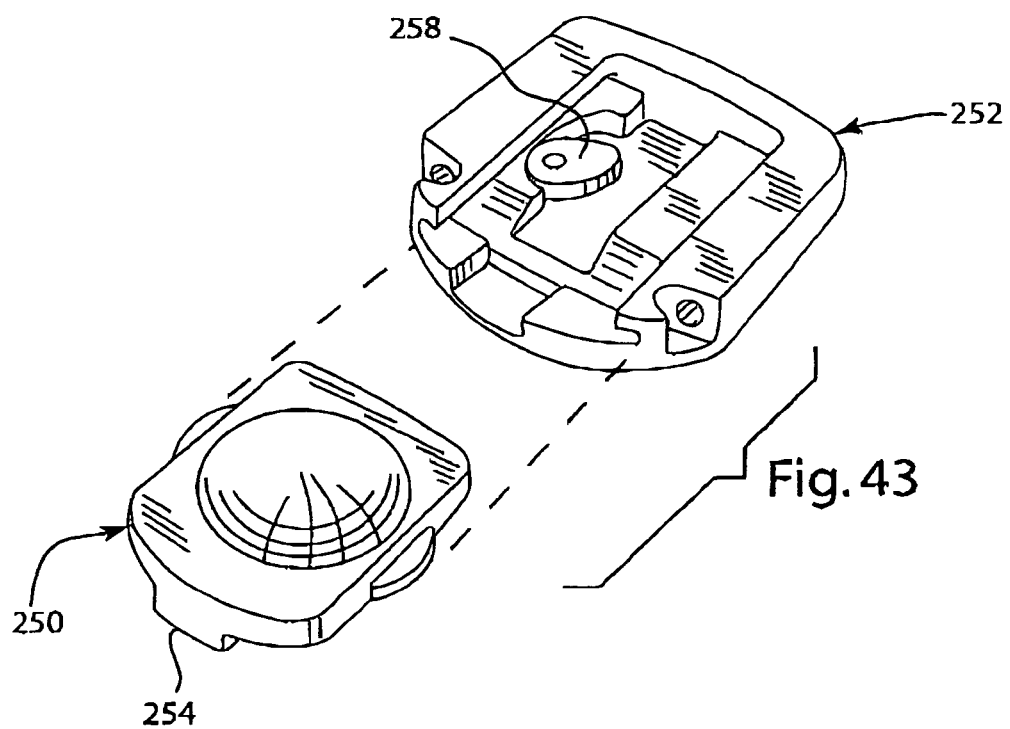
FIG. 43 is a top perspective view of an inlay and an endplate with a cam locking mechanism.
Figure 44:
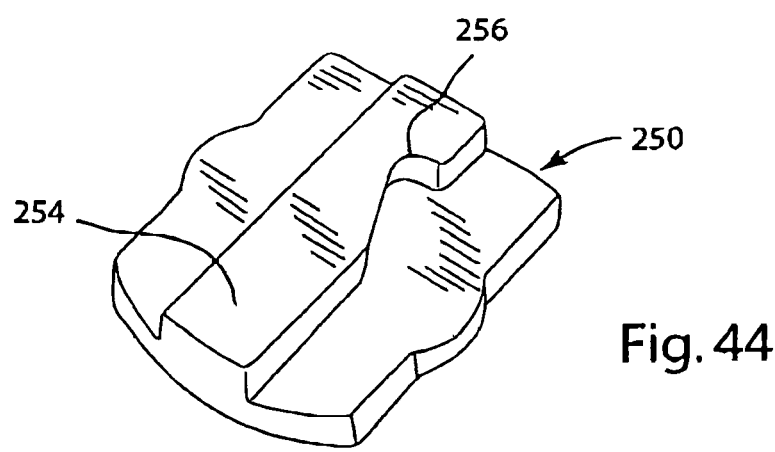
FIG. 44 is a bottom perspective view of the inlay depicted in FIG. 43.

Depicted in FIGS. 43-44 is a cam-like locking mechanism for an inlay 250 and an endplate 252. In this embodiment, inlay 250 is provided with a central strip 254 having a hook shaped cutout 256 near the rear end. Endplate 252 is then provided with a complementary shaped cam 258 which is resiliently biased toward central strip 254. As inlay 250 is inserted into endplate 252, cam 258 is initially pushed out of the way of central strip 254 until inlay 250 is fully seated and cam 258 is resiliently biased into cutout 256 to lock inlay 250 in place. If desired, a cam/cutout feature can also be provided on the other side of central strip 254 (as seen in FIGS. 51-52 below for a generally similar arrangement).

Figure 45:
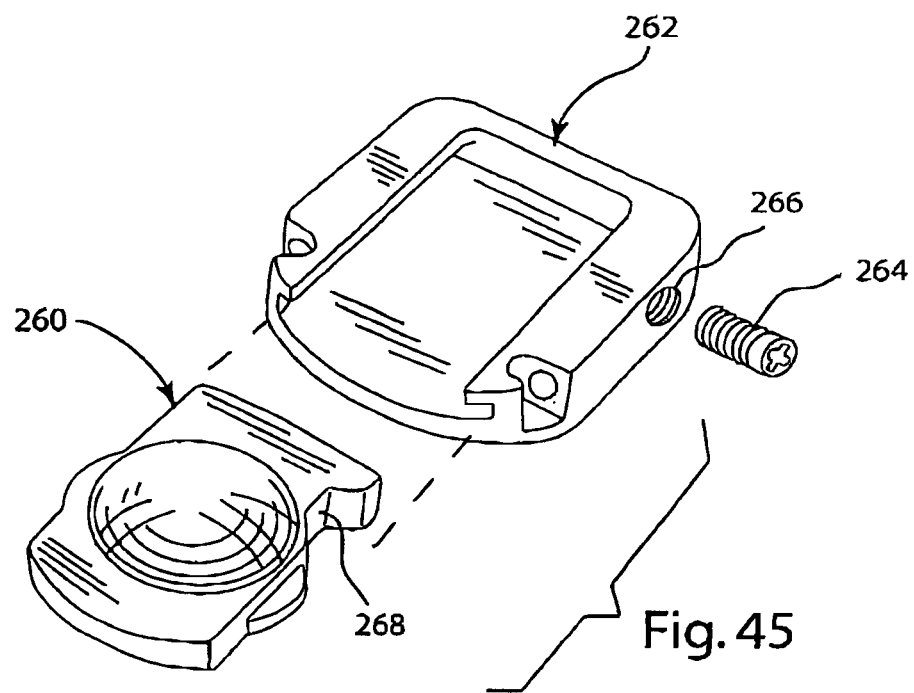
FIG. 45 is a top perspective view of an inlay in an endplate with a set screw locking mechanism.
Figure 46:
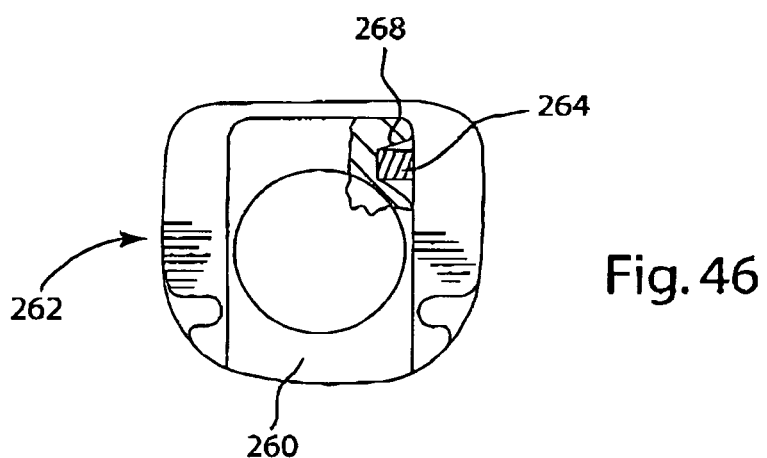
FIG. 46 is a bottom perspective view of the inlay depicted in FIG. 45 with the screw shown in a cut-away portion.

Depicted in FIGS. 45-46 is another embodiment using a screw, and in particular in which a set screw 264 is used to lock an inlay 260 in an endplate 262. In this embodiment, screw 264 is threadedly received in a screw hole 266 in one side of endplate 262, and when fully inserted to lock inlay 260 in place, screw 264 is received in a tapered cutout 268 provided in the adjacent side of inlay 260. Inlay 260 and endplate 262 are preferably secured together before insertion into an intervertebral space.

Figure 47:
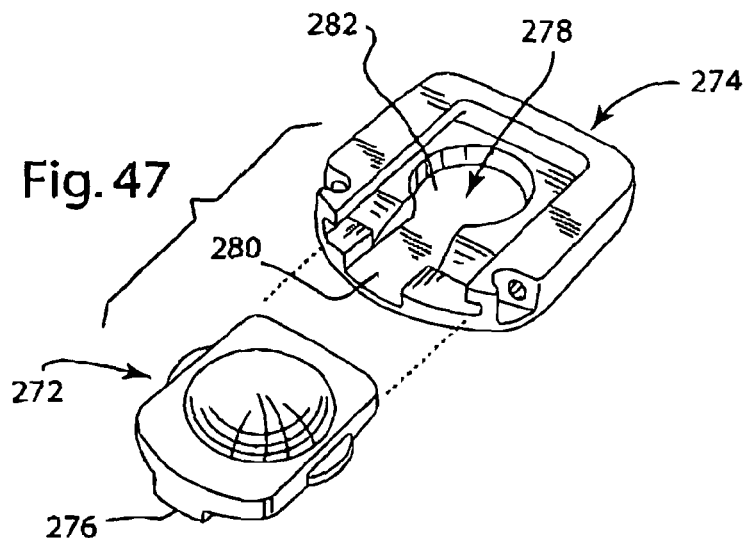
FIG. 47 is a top perspective view of an inlay in an endplate with a clip locking mechanism.
Figure 48:
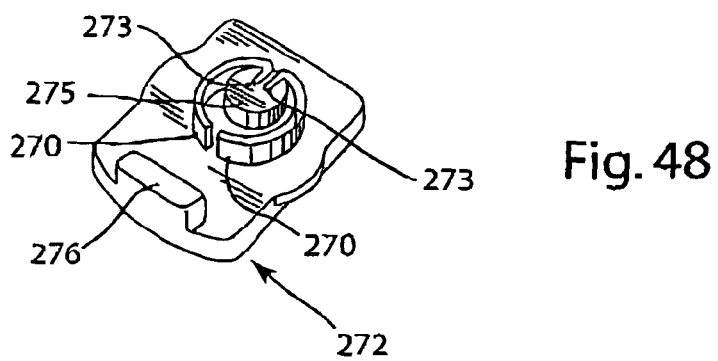
FIG. 48 is a bottom perspective view of the inlay depicted in FIG. 47.

Use of paired clip elements 270 to lock an inlay 272 to an endplate 274 is depicted in FIGS. 47-48. As shown, each clip element 270 is a semi-circular, resilient member secured as by a press fit at one end to a respective receiving slot 273 in a round protrusion 275 provided on the bottom surface of inlay 272. Inlay 272 also includes a frontward protrusion 276 so that inlay 272 preferably lays flat in a receiving portion 278 of endplate 274 when inserted therein. Receiving portion 278 includes an initial straight slot 280 which leads into a circular cutout 282. In operation, as the inlay 272 is inserted into the receiving portion 278, the clip elements 270 and the protrusion 274 slide along in the straight slot 280. Thereafter after front protrusion 276 is received into straight slot 280, clip elements 270 are resiliently received in circular cutout 282 to secure inlay 272 in endplate 274.

Figure 49:
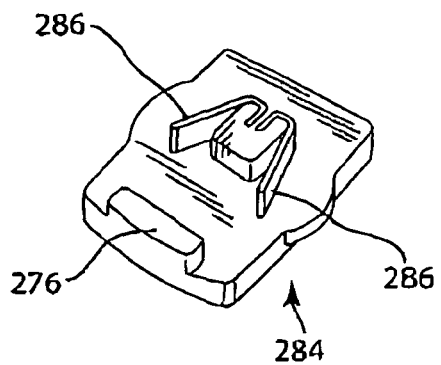
FIG. 49 is a bottom perspective view of an alternative embodiment of an inlay with a clip locking mechanism.

As an alternative to semi-circular clip elements 270, in an alternative embodiment depicted in FIG. 49, inlay 284 could be provided with angled clip elements 286 as shown. Such angled clip elements 286 are received in a rectangular cutout of an endplate (not shown) which would otherwise be similar to endplate 274.

Depicted in FIG. 50 is an embodiment of a locking mechanism which is similar to the finger locking mechanism discussed above and shown in FIGS. 12-14. In this embodiment, an inlay 288 is provided with long resilient fingers 290 along each side and ending in shoulders 292. During, but prior to full insertion, fingers 290 are pressed inwards into cutouts 294 in inlay 288. An endplate 296 is provided with cutouts 298 into which shoulders 292 will spring. In use, as inlay 288 is received in endplate 296, fingers 290 are pressed closely alongside the remainder of inlay 288, as shown by arrows 293, and shoulders 292 move into cutouts 294. When the inlay 288 is fully in place, the shoulders 292 spring outwardly and is trapped in the cutouts 298 of the endplate 296, thereby securing the inlay 288 in the endplate 296.

In FIGS. 51-52, a cam/cutout arrangement, generally similar to that of FIGS. 43-44, is depicted. In this embodiment, however, there are two cam/cutout arrangements. In addition, it will be appreciated that an inlay 300 includes a cutout 302 on each side which is made in the upper surface of inlay 300. Consequently, an endplate 304 includes resilient cams 306 on each side which mate with cutouts 302 and thus which are raised above a floor 309 of receiving portion 308. With this embodiment, after insertion of inlay 300 into endplate 304 and the location of cams 306 in cutouts 302, the correct positioning of cams 306 is visible and can be checked by the surgeon.

Depicted in FIGS. 53-54 is yet another way to lock and potentially make it easier to remove an inlay 310 from an endplate 312. In this embodiment, inlay 310 is provided with a central cutout 314 at the frontward end, and endplate 312 is provided with a channel through the front forming a deformable bridge 316. After inlay 310 is fully inserted into endplate 312, an osteotome or other instrument is inserted under bridge 316 and bridge 316 is deformed upwards into cutout 314 of inlay 310, thereby physically locking inlay 310 in endplate 312. Thereafter, if it is desired to remove inlay 310 from endplate 312, bridge 316 can be deformed back to its original position (and probably further) so that it no longer blocks movement of inlay 310 from coming out of endplate 312.

Depicted in FIG. 55 is a locking mechanism generally similar to that shown in FIG. 40. However, in this embodiment, an endplate 318 is provided with cutouts 319 housing respective spring members 320, which have a step portion 322. Step portions 322 are designed to cam over and then slide into cutouts 324 provided in an inlay 326 upon full insertion of inlay 326 into endplate 318.

Depicted in FIG. 56 is a positive locking mechanism utilizing screws 332. In this embodiment, an endplate 328 is provided with laterally movable locking members 330 which are positively cammed into place by advancement of screws 332 located in legs 334 of endplate 328. Inlay 336 is thus provided with cutouts 338 (only one of which is shown) into which locking members 330 are received once inlay 336 is fully inserted into endplate 328 and screws 332 are advanced to move locking members 330 into the respective cutouts 338. This embodiment is not limited to the inclusion of two screws 332, two cutouts 338 and two locking members 330; it being understood by one of ordinary skill that a single set of locking components could suffice to lock inlay 336 into endplate 328.

Another embodiment using spring members 342 as a locking mechanism generally similar to FIG. 55 is depicted in FIG. 57. In this embodiment, an endplate 340 is provided with small cutouts 341 housing V-shaped spring members 342, which includes free ends 344. Free ends 344 are designed to cam over and then snap into locking cutouts 346 provided in an inlay 348 upon full insertion of inlay 348 into endplate 340.

Depicted in FIGS. 58-60 is a locking mechanism with an additional spring or shim component as part of an inlay 354. In particular, an endplate 350 is generally similar to endplate 14 (FIG. 1) in that it has a detent recess 352. Inlay 354 is provided with a detent protrusion 356 for receipt in recess 352. However, in this embodiment, protrusion 356 is removable from inlay 354 by forming the free ends of protrusion 356 with suitable dovetail ridges 358 which are received in mating dovetail grooves 360 provided in inlay 354, as shown best in FIG. 60.

Depicted in FIGS. 61-62 is a crimping type of locking mechanism. In this embodiment, an endplate 362 is provided at the frontward end with short extensions 364 of lateral legs 363 formed by thinned portions. An inlay 366 is provided with cutouts 368 in which extensions 364 can be crimped using a suitable tool (not shown) when inlay 366 is fully inserted into endplate 362. After crimping into place, extensions 364 form a mechanism for positively and securely locking inlay 366 in endplate 362.

Another surgeon actuated locking mechanism is depicted in FIGS. 63-65. In this embodiment, an inlay 370 has a bottom cutout in which an L-shaped latch 372 is pivotably mounted and secured thereby to inlay 370. Latch 372 includes a short ridge 374, which rides along a front surface of inlay 370 until it is received and held in a notch 376 in the front of inlay 370. As evident from FIG. 65, inlay 370 is inserted in an endplate 378, which includes a resilient latching clip 380 mounted in a cutout 382, and which is designed to receive an end of latch 372. During insertion, latch 372 is in the position depicted in FIG. 63. However, after full insertion of inlay 372 into the receiving portion of endplate 378, latch 372 is moved by the surgeon from the unlatched position of FIG. 63 to the latched position of FIG. 64 where ridge 374 is located in notch 376. In addition, the movement of latch 372 to the latched position causes the other end of latch 372 to be captured behind clip 380.

Figure 66:
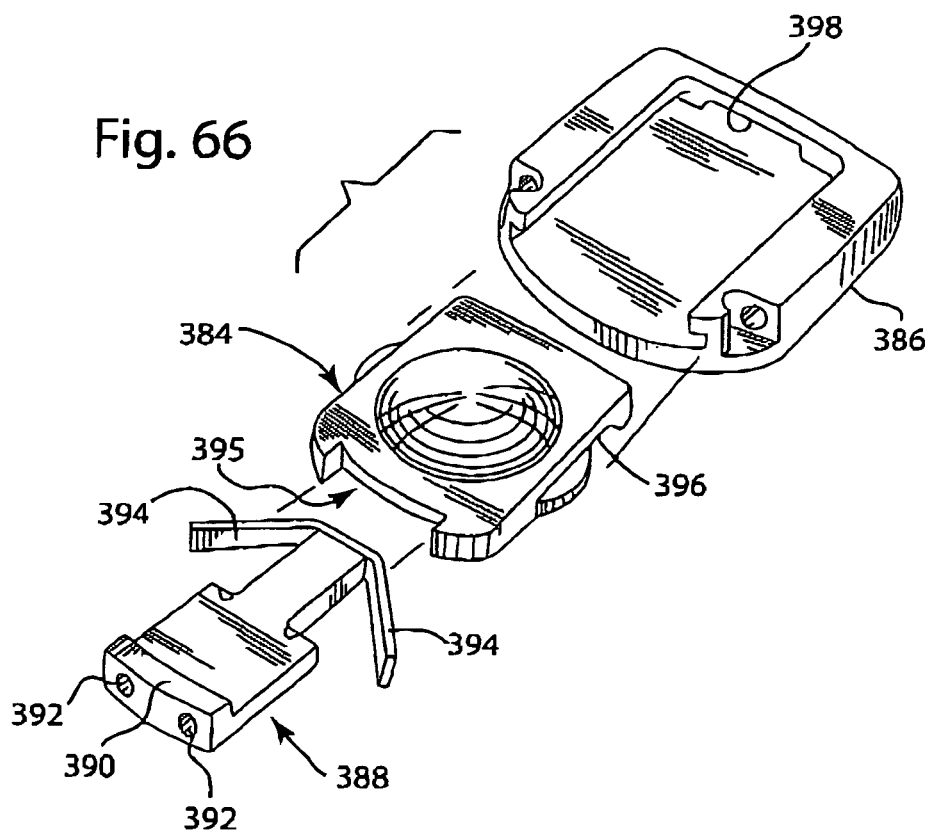
FIG. 66 is a top perspective view of an inlay in an endplate with a separate locking element.
Figure 67:
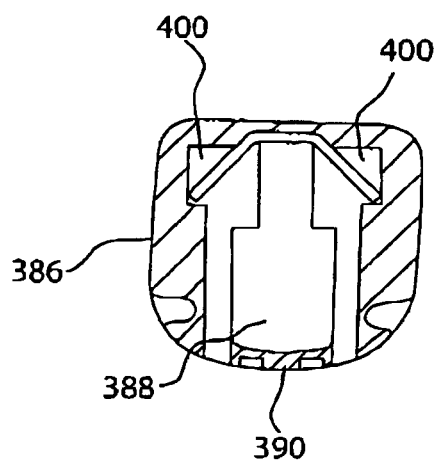
FIG. 67 is a cross sectional top perspective view with the inlay removed but with the locking element of FIG. 66 positioned to lock the inlay in the closed position in the endplate.

Depicted in FIGS. 66-67 is a locking mechanism whereby an inlay 384 is held in place in an endplate 386 by a separate locking element 388 which is later (or contemporaneously if desired) inserted into inlay 384 after full insertion thereof into endplate 386. Locking element 388 includes a front upstanding wall portion 390 in which holes 392 are provided so that locking element 388 is maneuverable by a suitable instrument (not shown). At the rearward end, locking element 388 includes opposed arms 394 resiliently mounted in the position shown in FIG. 66. Inlay 384 includes a front cutout 395 into which wall portion 390 is matingly received, and a lower surface cutout into which the remainder of locking element 388 is slidably received and which will push arms 394 generally parallel to each other as locking element 388 is inserted into endplate 386. This lower surface cutout includes lateral openings 396 though which arms 394 spring out when they reach a mounted position. Endplate 386 includes a rear cutout 398 into which the rearward end of locking element 388 is received as shown in FIG. 67, as well as arm cutouts 400 into which arms 394 are ultimately received. In operation, endplate 386 is implanted, and inlay 384 is then inserted somewhat loosely into endplate 386, but captured by the legs of endplate 386. Thereafter, locking element 388 is inserted between endplate 386 and inlay 384 and pushed until all of the following occur as depicted in FIG. 67 (note, inlay 384 is not shown in this figure): wall portion 390 abuts front cutout 395, the rear of locking element 388 is located in rear cutout 398, and arms 394 spring out through lateral openings 396 and are held in place in arm cutouts 400. In this position, all three elements, inlay 384, endplate 386 and locking element 388, are secured together and to each other.

Depicted in FIGS. 68-69 is another spring-actuated locking mechanism, generally similar to that shown in FIGS. 41-42, but this locking mechanism is provided with a second locking mechanism to assure proper locking of the first mechanism and to secure the first mechanism in place. In this embodiment, an inlay 402 is provided on its underside with separate integral resilient arms 404, which are conveniently cut from the block forming inlay 402. Each arm 404 has a catch shoulder 406. Arms 404 are received in a mating channel 408 of an endplate 410, which forms a catch 411 for catch shoulders 406. In addition, there is a central lock channel 412 formed between arms 404, in which a lock bar 414 is receivable. As shown in FIG. 69, lock bar 414 is received in lock channel 412 and is then held in place by the interaction of notches 416 in the sides of lock bar 414 and corresponding teeth 418 provided on arms 404. In operation, arms 404 are initially pushed resiliently together as they enter a guiding portion of channel 408, but eventually arms 404 spring outwards and shoulders 406 are captured by catches 411 of channel 408. Thereafter, lock bar 414 is pushed into lock channel 412 until notches 416 are engaged by teeth 418. In this position, arms 404 are generally prevented from any movement in a central direction, which might tend to allow arms 404 to slip past catches 411 and hence for inlay 402 to be removed from endplate 410. However, since teeth locking lock bar 414 are small, lock bar 414 can be removed fairly easily if desired, though it will not otherwise move unless a positive force is suitably provided. Once lock bar 414 is removed, then arms 404 would be permitted to move under sufficient force and inlay 402 could be withdrawn.

Figure 71:
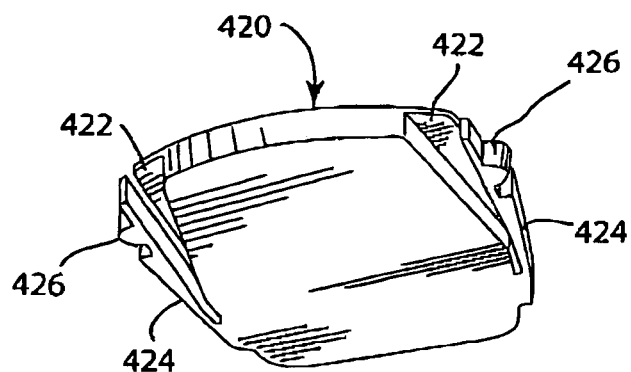

Depicted in FIGS. 70-71 is an inlay 420 which is received in a suitable endplate (not shown). Inlay 420 includes guide strips on each side for guiding inlay 420 into the associated endplate, which guide strips are formed into two parts, an upper ledge 422 and a resilient arm 424. Each arm 424 is attached at the rearward end thereof, and includes a tooth 426 facing laterally outward as shown. Ledge 422 is shaped so that at the frontward end, arm 424 can be resiliently received thereunder. In operation, as inlay 420 is pushed into a receiving endplate, ledge 422 locks inlay 420 in place as ledge 422 is guided by the guide grooves of the endplate. As inlay 420 is pushed further in, arms 424 are resilient moved inwards under ledges 422 as teeth 426 ride along the guide groove, until inlay 420 is fully inserted. At that time, teeth 426 move outward into corresponding cutouts provided in the guide grooves to securely lock inlay 420 in place.

Figure 72:
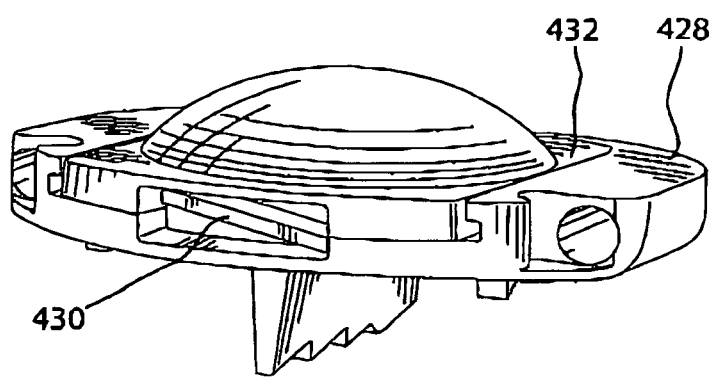
FIG. 72 is a top perspective view of an endplate and inlay where a bendable arm of the endplate forms a locking mechanism.

As noted above in discussing FIGS. 53-54, a portion of an endplate can be moved into position to block an inlay from moving out of position in the endplate. Depicted in FIG. 72 is another embodiment of such a design, in which an endplate 428 is provided with an arm 430 located in a cutout in the frontward end and connected at one lateral side to endplate 428. As shown in the figure, arm 430 can be bent upwards into a complementary cutout of a front portion of an inlay 432 to engage and lock inlay 432 fully inserted in endplate 428. Arm 430 can be used in conjunction with other locking mechanisms as shown herein as well if it is desired for arm 430 to serve as a second locking mechanism rather than a primary locking mechanism.

Figure 73:
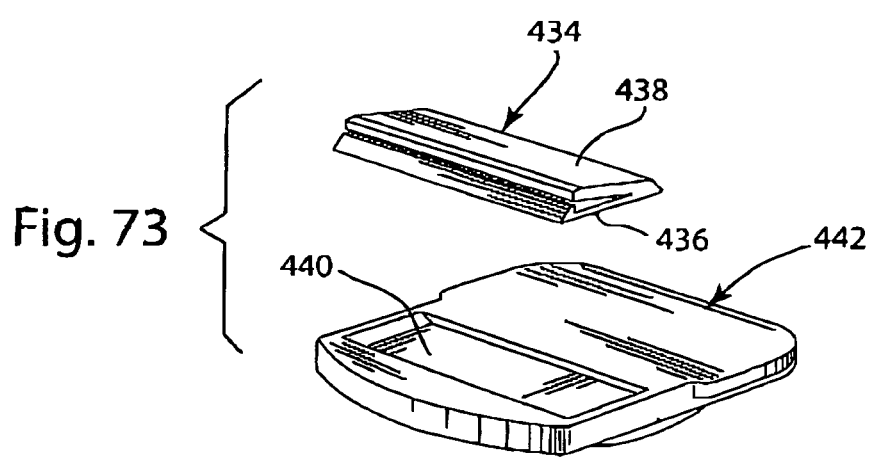
FIG. 73 is a bottom perspective view of an inlay with a V-shaped ramp used to form a locking mechanism.

If it is desired to provide a greater resilience to a ramp on an inlay, such as ramp or guide protrusion 46 discussed above, an alternative ramp 434 as depicted in FIG. 73 is provided. As shown, ramp 434 has a V-shape, so that it forms a base portion 436 and a lock portion 438. Base portion 436 is trapped in cutout 440 in inlay 442 by the dovetail shape of the edges. Lock portion 438 is then left to resiliently ride along the receiving portion of the endplate until it is resiliently moved into the corresponding detent recess of the endplate as discussed in various embodiments above.

Figure 74:
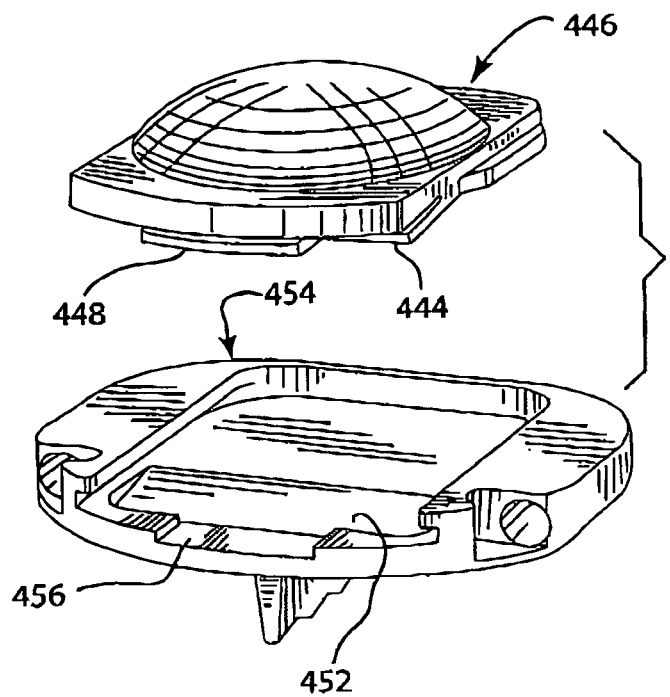
FIG. 74 is a top perspective view of an inlay and endplate where the locking mechanism includes an extending tab.
Figure 75:
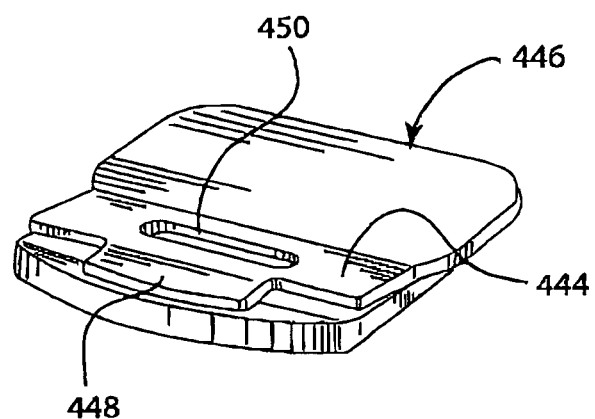
FIG. 75 is a bottom perspective view of the inlay depicted in FIG. 74.

Depicted in FIGS. 74-75 is an embodiment of a locking mechanism in which a ramp 444 provided on an inlay 446 includes an extending tab 448. Ramp 444 includes a central slot 450 therein, so that ramp 444 is somewhat resiliently mounted to inlay 446. Besides a receiving cutout 452 for the ramp 444, an endplate 454 includes a tab cutout 456 in which the tab 448 is ultimately received. In operation, when inlay 446 is fully received in endplate 454, with ramp 444 received in receiving cutout 452, tab 448 is also located in tab cutout 456, but in a position where tab 448 is pushed upwards and is preferably flush against both tab cutout 456 and the adjacent portion of inlay 446 thus showing that inlay 446 is fully inserted. The action of ramp 444 being resiliently received in receiving cutout 450 may also provide a snapping sound and tactile feel to alert the surgeon that reception has taken place.

Figure 76:
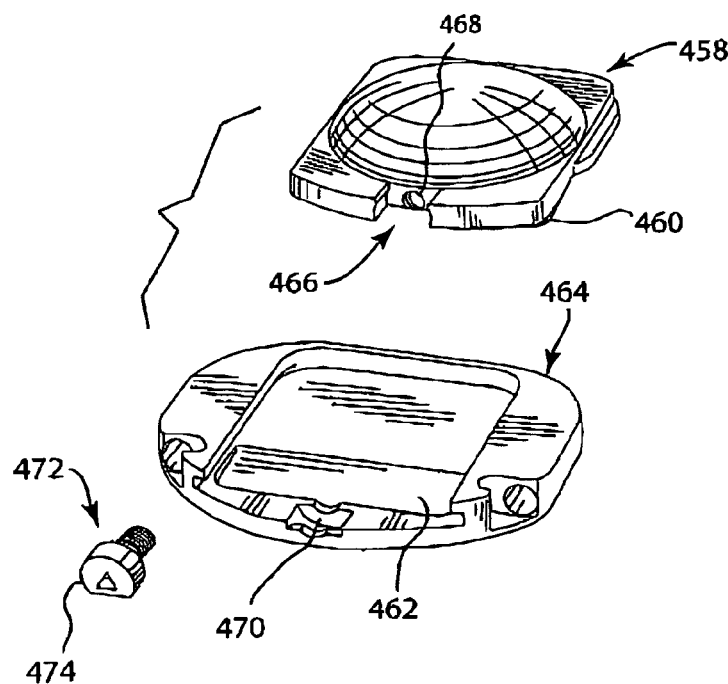
FIG. 76 is a top perspective view of an inlay and endplate provided with a camming member as a secondary locking mechanism.
Figure 77:
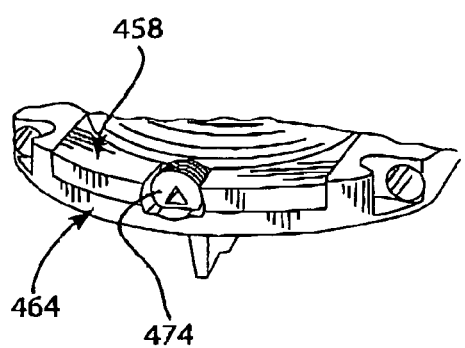
FIGS. 77 and 78 are partial top perspective views with the rear portions cut away of the inlay and endplate depicted in FIG. 76 showing the camming member in the non-locking and locking positions respectively.
Figure 78:
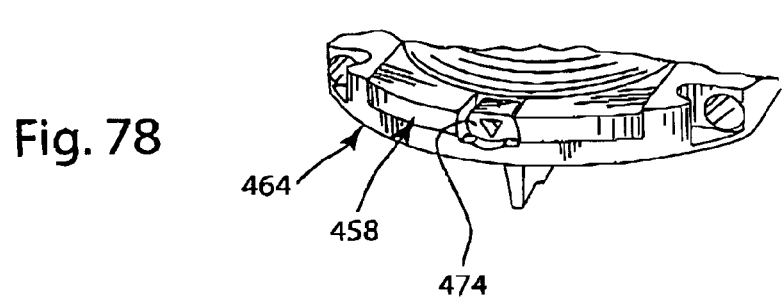

Depicted in FIGS. 76-78 is another embodiment where a secondary locking mechanism is used together with a primary locking mechanism. In this embodiment, an inlay 458 is provided with a ramp 460 which is received in a corresponding cutout 462 in an endplate 464. In addition, the inlay 458 is provided with a front cutout 466 leading into a hole 468; while the endplate 464 is provided with a semi-circular slot 470 with small longitudinal cutouts on either side of the slot 470. As shown in FIG. 77, when inlay 458 is fully received in endplate 464, and hence ramp 460 is trapped in cutout 462, a camming member 472, with a flat sided head 474 thereof, is inserted above slot 470 (with the flat side down so it will fit) and into hole 468 of inlay 458. Thereafter, using a suitable tool (not shown), camming member 472 is rotated 180° to cause the curved portion of head 474 to be trapped in slot 470, as shown in FIG. 78, providing a secondary locking mechanism.

Depicted in FIGS. 79-80 is an embodiment where the locking mechanism uses a threaded screw 476. Screw 476 is received in a threaded hole or slot 478 provided in a slotted guide 480 provided in a receiving portion of an endplate 482. An inlay 484 is thus complementary shaped and includes a depending projection 486, which is matingly received in slotted guide 480. In operation, after inlay 484 is fully inserted into endplate 482, with projection 486 thus located in the rearward or distal end of slotted guide 480, screw 476 is screwed down into threaded slot 478 so that the rearward end of screw 476 contacts the frontward end of projection 486 to securely lock inlay 484 in endplate 482.

Another embodiment using screws 488 to lock an inlay 490 in an endplate 492 is depicted in FIGS. 81-82. In this embodiment, screws 488 are received in threaded holes 494 provided next to guide grooves 496 of endplate 492. Inlay 490 is then provided with wings 498 having a frontward facing edge 500 as shown. In operation, after inlay 490 is fully inserted in endplate 492, with wings 498 located in the rearward or distal end of guide grooves 496, screws 488 are screwed down into threaded holes 494 so that the rearward ends of screw 476 contact respective edges 500 of wings 498 to securely lock inlay 490 in endplate 492.

Depicted in FIGS. 83-84 is an embodiment in which the locking mechanism is provided by a separate spring clip 502, which engages both an inlay 504 and an endplate 506. In this embodiment, inlay 504 is provided with a clip receiving area 508 and lateral steps 510 in each lateral side near the front of receiving area 506. Endplate 506 is similarly constructed, with a clip receiving area 512 in the receiving portion for inlay 504 and lateral steps 514 in each lateral side near the front of receiving area 512. It will thus be appreciated that spring clip 502 includes upper lateral flanges 516 and lower flanges 518. In operation, after inlay 504 is fully inserted in endplate 506, spring clip 502 is then longitudinally inserted into receiving areas 508 and 512, which now form a common opening. When spring clip 502 is fully inserted, upper flanges 516 resiliently move and are trapped behind lateral steps 510 of inlay 504, and lower flanges 518 resiliently move and are trapped behind lateral steps 514 of endplate 506. Spring clip 502 thus securely locks inlay 504 against movement out of endplate 506; and since spring clip 502 is resilient, it can later be removed if desired.

Figure 85:
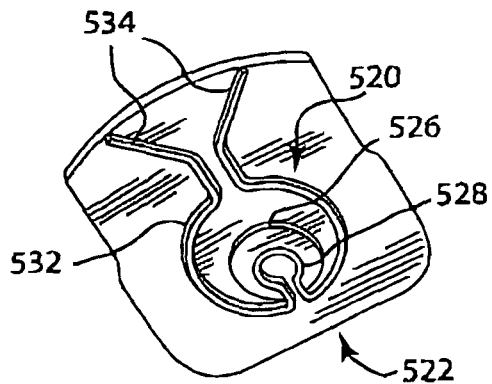
FIG. 85 is a bottom perspective view of an inlay and associated locking clip.
Figure 86:
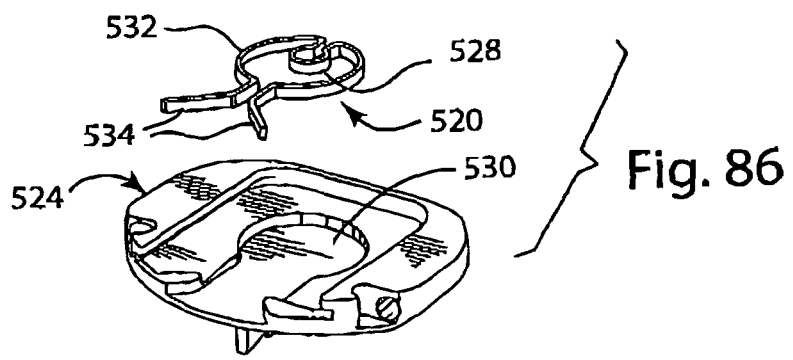
FIG. 86 is a top perspective view of an endplate and associated locking clip of FIG. 85 which receives the inlay of FIG. 85 and which is held in place by the locking clip.

Depicted in FIGS. 85-86 is another embodiment of a locking mechanism making use of a spring clip 520 to engage an inlay 522 to an endplate 524. In this embodiment, inlay 522 includes a ring 526 projecting from the bottom surface thereof, which ring 526 is open at the rearward end. As shown in FIG. 85, spring clip 520 is thus attached to ring 526 by use of a resilient open ring portion 528, which resiliently fits into ring 526. Endplate 524 is provided with a cutout 530 in a receiving portion thereof which is designed to resiliently receive an outer open ring portion 532 of spring clip 520 when legs 534 of spring clip 520 are resiliently brought together. In operation, as inlay 522 with spring clip 520 attached thereto is received in the receiving portion of endplate 524, outer ring portion 532 is compressed and thus fits into cutout 530, with outer ring portion 532 resiliently moving outward to matingly fit into cutout 530 when inlay 522 is fully inserted. At that time, legs 534 extend along the mating side walls of cutout 530, and can be brought together and thus used to pull inlay 522 and spring clip 520 out of endplate 524, if so desired.

Figure 87:
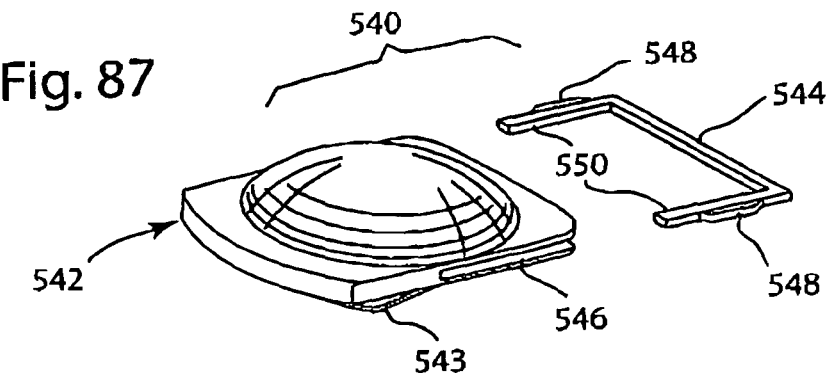
FIG. 87 is a top perspective view of an inlay with a retaining ring having wings.

Depicted in FIG. 87 is an inlay 540 which is generally similar to inlay 16 discussed above. However, in this embodiment, inlay 16 is made of two parts, a base part 542 and a retaining ring 544. Base part 542 includes a ramp 543 (like inlay 16). Base part 542 also includes side grooves 546 (only one of which is shown) in order to mount retaining ring 544 thereon to form the complete inlay 540. Retaining ring 544 includes wings 548 on each leg 550 which legs 550 are frictionally or otherwise securely received in respective grooves 546. By use of retaining ring 544, as assembled inlay 540 is guided into the guiding grooves of an associated endplate (such as endplate 14), wings 548 deflect and allow insertion as ramp 543 slides along the receiving portion of the endplate and drops into the pocket. The use of retaining ring 544 is that it allows wings 548 (and the hence the remainder of retaining ring 540) to be made of a more (or less) elastic material then base part 542, so that wings 548 could allow for more deflection if desired. Retaining ring 540 could be of materials such PE, Nitinol, or other material that would deflect to allow insertion.

In the above embodiments, various springs or resiliencies have been noted for locking various elements in place. It will be appreciated that the force of such springs or resiliency is adjustable as desired to increase the locking force if required; or to decrease the locking force making removal of the held element easier. It will also be appreciated that various ones of the locking mechanisms will provide a tactile or hearing sensation when the inlay is fully inserted into the endplate, as by parts snapping, springing or otherwise being captured in place.

The use of primary and secondary locking mechanisms has been discussed above for some embodiments. However, it will be appreciated that most any combination of locking mechanisms can be used to provide primary and secondary (and even tertiary) locking mechanisms as desired.

Various advantageous features have been described above with respect to various embodiments. Such advantageous features are also considered to be usable together, rather than singly as typically depicted and described.

While the present invention has been described with respect to exemplary embodiments thereof, it will be understood by those of ordinary skill in the art that variations and modifications can be effected within the scope and spirit of the invention.

We claim:

1. An intervertebral implant configured to be mounted between a superior vertebra and an inferior vertebra, the implant comprising:
an endplate defining a front end, a rear end, an outer surface that is configured to engage a vertebra, the endplate further including an inner surface opposite to the outer surface, the endplate further defining a cutout that extends into the inner surface;
an inlay defining a proximal end, a distal end, an engagement surface, and an exposed surface, wherein the engagement surface slides along the inner surface of the endplate such that the distal end moves toward the rear end to couple the inlay to the endplate, the inlay further including a resilient member, the resilient member configured to be received in the cutout so as to couple the inlay to the endplate, and the proximal end does not extend over an entirety of the resilient member, thereby allowing visualization of at least a portion of the resilient member when the resilient member is received in the cutout; and
an insert configured to be mounted to the inlay and having an articulating surface.

2. The intervertebral implant of claim 1, wherein the insert is a first insert, the articulation surface is a first articulation surface, the first articulation surface is made of a first material, and the intervertebral implant further comprises a second insert configured to be mounted in the inlay, the second insert having a second articulation surface that is made of a second material that is different from the first material.

3. The intervertebral implant of claim 2, wherein the first material is a ceramic material and the second material is a polyethylene/metal material.

4. The intervertebral implant of claim 1, wherein the endplate is a first endplate and the intervertebral implant further comprises:
a second endplate having an inner surface and an outer surface, the outer surface of the first endplate configured to engage the inferior vertebra, and the outer surface of the second endplate configured to engage the superior vertebra and the second endplate further having an inner surface that mates with the articulation surface of the insert such that the second endplate can articulate with respect to the insert.

5. The intervertebral implant of claim 1, further comprising:
a recess at least partially defined by the inner surface, the recess disposed between the front end and the rear end of the endplate, the recess configured to receive the inlay, and wherein the cutout is disposed next to the front end; and the resilient member is a resilient ramp configured to be received in the cutout such that the resilient ramp resists movement of the inlay toward the front end when the resilient ramp is positioned in the cutout.

6. The intervertebral implant of claim 2, further comprising:
a through hole defined in the inlay and extending between the engagement surface and the exposed surface, wherein the first and second inserts are configured to be mounted in the through hole such that the first and second articulating surfaces are located close to the exposed surface, respectively.

7. An intervertebral implant configured to be inserted into an intervertebral space between a superior vertebra and an inferior vertebra, the implant comprising:
an endplate defining a front end and an opposed rear end, and an inner surface and an opposed outer surface, the outer surface configured to engage the superior vertebra or the inferior vertebra, the endplate defining a cutout that extends into the inner surface; and
an inlay defining a proximal end and a distal end that is spaced from the proximal end along a direction of insertion of the intervertebral implant into the intervertebral space, said inlay defining an exposed surface, an engagement surface opposite the exposed surface, the inlay further including a resilient member, the resilient member configured to be received in the cutout so as to couple the inlay to the endplate, wherein the proximal end does not extend over an entirety of the resilient member, thereby allowing visualization of at least a portion of the resilient member when the resilient member is received in the cutout.

8. The intervertebral implant of claim 7, wherein the endplate includes a first tapered surface formed in the recess and positioned close to the rear end of the endplate, and the inlay includes a second tapered surface that is positioned closer to the distal end than to the proximal end of the inlay and the second tapered surface mates with the first tapered surface.

9. The intervertebral implant of claim 8, wherein the first tapered surface extends in a direction from the front end toward the rear end of the endplate, the first tapered surface defining at least sides of the recess, and the second tapered surface extends in a direction from the proximal end toward the distal end at sides of the inlay.

10. The intervertebral implant of claim 7 wherein the resilient member is a resilient ramp secured to the engagement surface of the inlay, and
the resilient ramp is configured to be received in the cutout such that micromotion between the inlay and the endplate is limited.

11. The intervertebral implant of claim 7, wherein the inlay defines at least one side edge, the resilient member including fins disposed along the at least one side edge, the inlay defining at least one inner side surface and grooves that extend into the at least one inner side surface, and the fins are configured to be positioned in the grooves to secure the inlay to the endplate.

12. The intervertebral implant of claim 7, further comprising:
an insert configured to be mounted to the inlay, wherein the inlay defines a through hole, and the insert is configured to be received in the through hole.

13. An intervertebral implant configured to be mounted between a superior vertebra and an inferior vertebra, the implant comprising:
an endplate defining a front end and an opposed rear end, an inner surface and an opposed outer surface, the outer surface configured to engage a vertebra, the endplate including a recess that is at least partially defined by the inner surface, the endplate further defining a cutout that extends into the inner surface; and
an inlay defining a proximal end and an opposed distal end, an engagement surface and an opposed exposed surface, the inlay further including a resilient ramp that extends from the engaging surface, the resilient ramp defining a root end, a terminal end that is spaced from the root end, a lower surface positioned to face the inner surface of the endplate, and an opposed upper surface that is spaced from the exposed surface, wherein the engagement surface is configured to slide along the inner surface so as to position the inlay in the recess until the terminal end is received in the cutout so as to couple the inlay to the endplate, wherein the exposed surface does not extend over an entirety of the terminal end.

14. The intervertebral implant of claim 13, wherein the terminal end of the resilient ramp is positioned closer to the proximal end than to the distal end of the inlay.

15. The intervertebral implant of claim 13, wherein a first width of the inlay at the proximal end is less than a second width of the inlay at the distal end.

16. The intervertebral implant of claim 13, wherein the resilient member is comprised of a leaf spring which is hinged at the root end to the engagement surface.

17. The intervertebral implant of claim 13, wherein the resilient member is comprised of a pair of resilient ramps positioned on either side of the inlay next to the proximal end, and the cutout is comprised of a pair of cutouts positioned at sides of the recess, the pair of resilient ramps configured to be received in the pair of cutouts to limit movement of the inlay toward the front end of the endplate.

18. The intervertebral implant of claim 13, wherein a top edge of the resilient member is generally coplanar with the exposed surface of the inlay when the inlay is coupled to the endplate.

19. The intervertebral implant of claim 13, wherein the endplate includes a crosspiece at the rear end and two legs that are disposed at sides of the endplate along a direction from the front end toward the rear end, the crosspiece and the legs cooperate to define the recess, and the distal end of the inlay is configured to face the crosspiece when the inlay is coupled to the endplate.

20. The intervertebral implant of claim 13, wherein the resilient member is configured such that it creates an audible sound when the resilient member is received by the cutout as the inlay is inserted in the recess.

21. The intervertebral implant of claim 1, wherein the inlay defines a lateral edge that is disposed along a direction from the proximal end toward the distal end, the inlay including at least one wing that is disposed along at least a portion of the lateral edge, and the endplate defines a lateral portion that is disposed along a direction from the rear end toward the front end, the endplate including at least one rail disposed along at least a section of the lateral portion, the at least one rail configured to receive the at least one wing to secure the inlay to the endplate.

22. The intervertebral implant of claim 1, wherein the inlay defines a lateral edge, and the resilient member includes fingers that extend from the lateral edge.

23. The intervertebral implant of claim 1, wherein the resilient member is a protrusion that extends from the engagement surface.

24. The intervertebral implant of claim 1, wherein the resilient member includes resilient arms.

25. The intervertebral implant of claim 1, wherein the resilient member is a clip element that is configured to be press fitted in the cutout.

26. The intervertebral implant of claim 1, wherein the clip element has a substantially semi-circular shape.

27. The intervertebral implant of claim 1, wherein the inlay includes a tab that is disposed closer to the proximal end than to the distal end, the tab defining a laterally reduced portion such that the exposed surface does not extend over the entirety of the terminal end.

28. The intervertebral implant of claim 2, wherein the first material is a metallic material, and the second material is a polyethylene.

29. The intervertebral implant of claim 7, wherein the endplate further defines a recess that is at least partially defined by the inner surface.

30. The intervertebral implant of claim 7, wherein the inlay further includes a tab that is disposed closer to the proximal end than to the distal end, the tab defining a laterally reduced portion such that the exposed surface does not extend over the entirety of the terminal end.

31. The intervertebral implant of claim 13, wherein the exposed surface does not extend over an entirety of the terminal end so as to allow visualization of the upper surface of the resilient member at the terminal end when the resilient member is received in the cutout.

32. The intervertebral implant of claim 31, wherein the endplate defines a recess that overlaps the terminal end when the resilient member is received in the cutout.

* * * * *